United States Patent [19]
Campbell et al.

[11] Patent Number: 5,409,483
[45] Date of Patent: Apr. 25, 1995

US005409483A

[54] DIRECT VISUALIZATION SURGICAL PROBE

[75] Inventors: Peter Campbell, Milpitas, Calif.; Jeffrey H. Reese, 35 Tulip La., Palo Alto, Calif. 94301; Daren L. Stewart, Redwood City, Calif.

[73] Assignee: Jeffrey H. Reese, Palo Alto, Calif.

[21] Appl. No.: 62,384

[22] Filed: May 14, 1993

Related U.S. Application Data

[63] Continuation-in-part of Ser. No. 989,098, Jan. 22, 1993.

[51] Int. Cl.⁶ .............................................. A61B 17/36
[52] U.S. Cl. .................................... 606/15; 606/13; 607/89
[58] Field of Search ...................................... 606/13-17, 606/194, 192, 7; 604/20, 21; 128/395-398, 4, 6; 607/88, 89

[56] References Cited

U.S. PATENT DOCUMENTS

| 4,676,231 | 6/1987 | Hisazumi et al. | 606/14 |
| 4,784,133 | 11/1988 | Mackin | 606/7 |
| 4,830,460 | 5/1989 | Goldenberg | 606/15 |
| 4,967,745 | 11/1990 | Hayes et al. | 606/14 |
| 4,998,930 | 3/1991 | Lundahl | |
| 5,007,437 | 4/1991 | Sterzer | 607/138 |
| 5,092,841 | 3/1992 | Spears | 606/194 |
| 5,188,634 | 2/1993 | Hussein et al. | 606/7 |
| 5,190,540 | 3/1993 | Lee | 606/192 |

OTHER PUBLICATIONS

Fujisawa, et al., "Nd:YAG Laser Irradiation to Intraluminal Mass Lesions of the Superior Vena Cava Under Laser Balloon Angioscopy in an Experimental Canine Model", Japanese Journal of Surgery, vol. 20, No. 4, pp. 411-417, 1990.
Ischinger, et al., "Laser Balloon Angioplasty: Technical Realization and Vascular Tissue Effects of a Modified Concept", Lasers in Surgery and Medicine 10:112-123 (1990), Wiley-Liss, Inc.
Okada, et al., "Balloon Cystoscopy with Neodymium-:YAG Laser", The Journal of Urology, vol. 148, 285-288, Aug. 1992.
Panjehpour, et al., "Centering Balloon to Improve Esophageal Photodynamic Therapy", Lasers in Surgery and Medicine 12:631-638 (1992), Wiley-Liss, Inc.

Primary Examiner—Stephen C. Pellegrino
Assistant Examiner—Michael Peffley
Attorney, Agent, or Firm—Haynes & Davis

[57] ABSTRACT

A surgical probe for use in a hollow vessel or other region of the body which comprises a multi-lumen catheter having a transparent, non-compliant balloon coupled to the distal end, such that the balloon has a known shape when inflated. A direct visualization scope is provided in a first lumen of the multi-lumen catheter providing direct visualization into the hollow vessel through the non-compliant balloon. An adapter is coupled to a second lumen of the multi-lumen catheter near the proximal end to supply a transparent fluid through the second lumen to inflate the balloon to the predefined shape. In this aspect, the balloon operates to clear the scope tip by pressing tissue on the walls of the hollow vessel out of the way of the end of the scope. This provides the user of the device a consistent clear view of the tissue at the tip of the scope. A fiber optic is provided in a third lumen of the multi-lumen catheter to deliver light energy to the hollow vessel through the non-compliant balloon. A mechanism is provided for positioning the light emitting tip of the fiber optic within the balloon to establish a known propagation distance to the surface of the balloon for the light energy emitted from the light emitting tip.

38 Claims, 16 Drawing Sheets

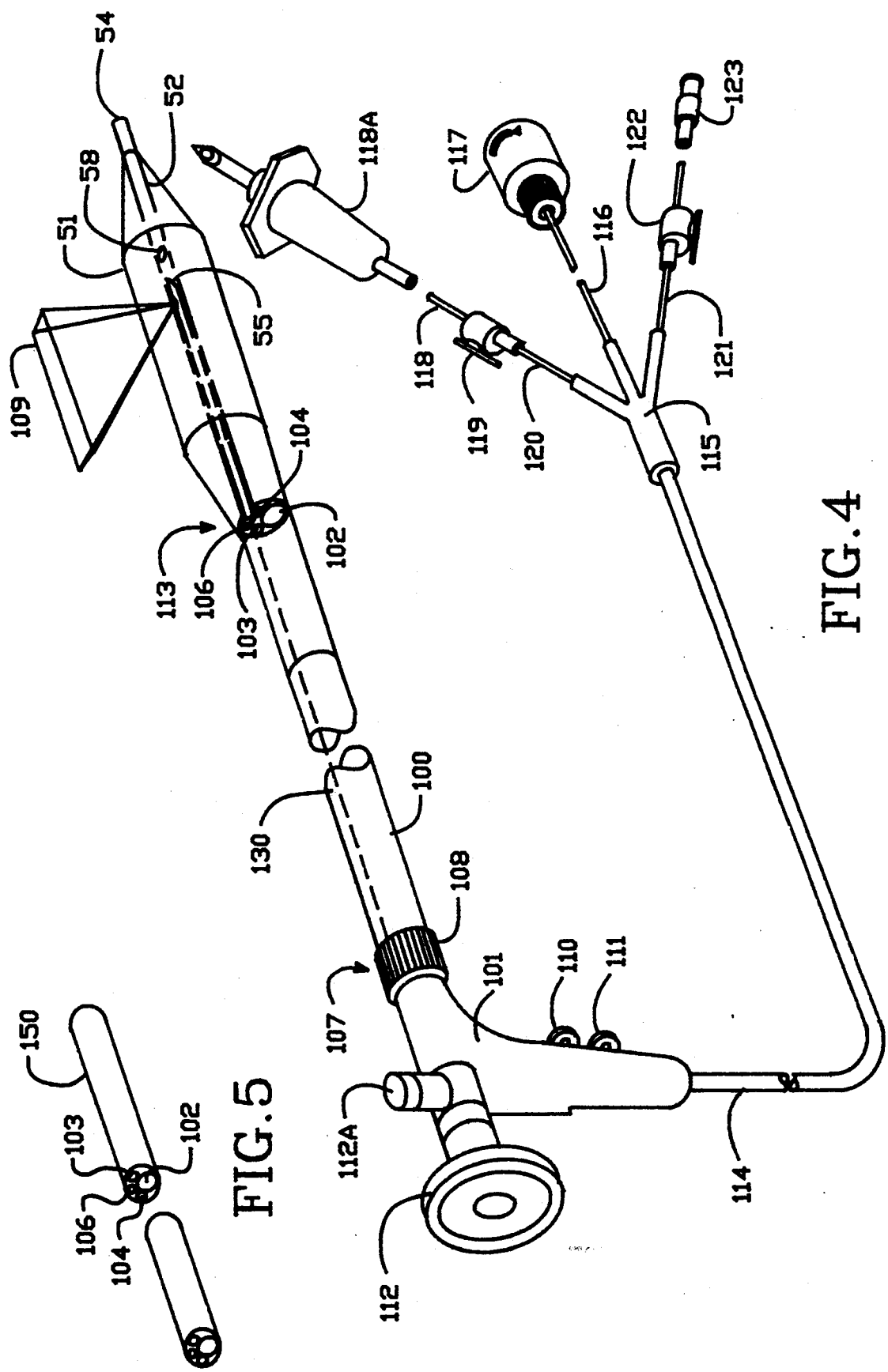

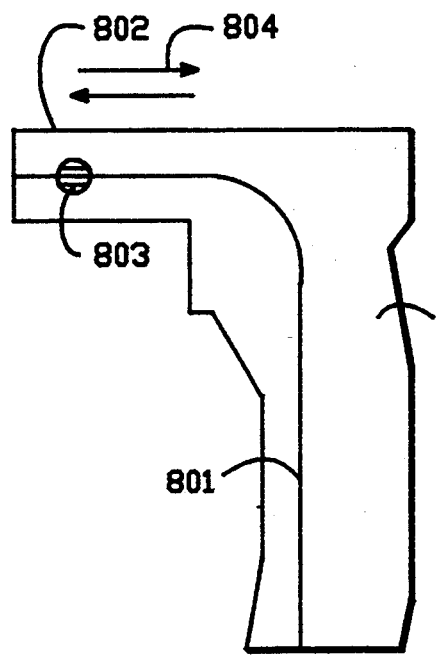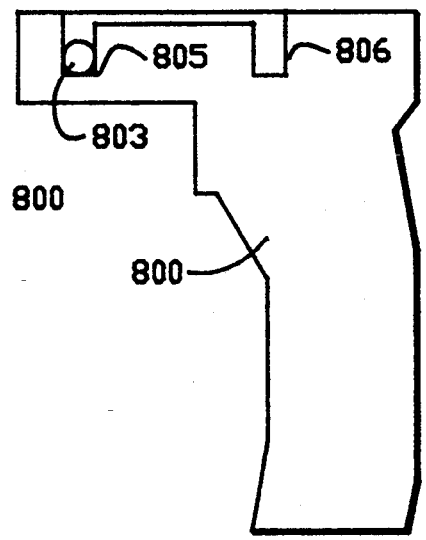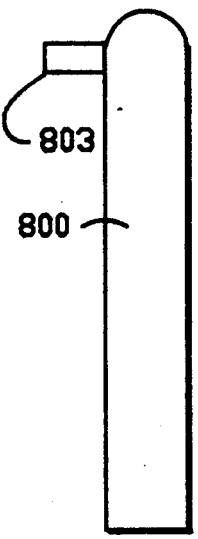
FIG.13A  FIG.13B  FIG.13C
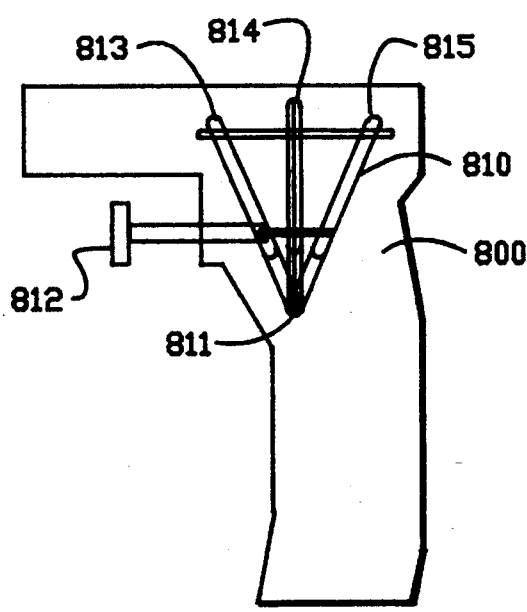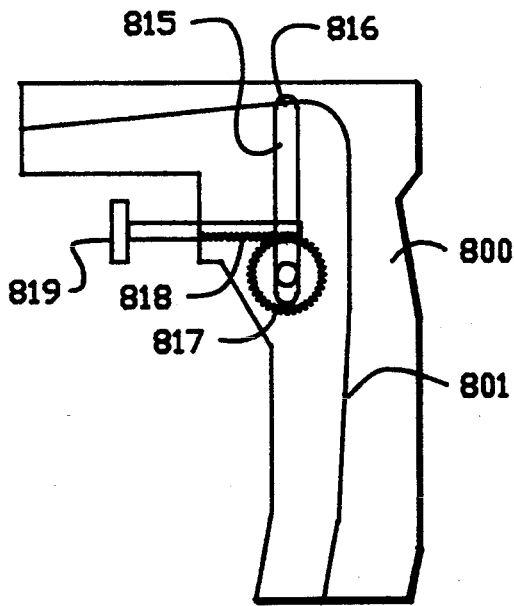
FIG.14  FIG.15

SECTION A-A

DIRECT VISUALIZATION SURGICAL PROBE

The present application is a continuation-in-part of U.S. patent application Ser. No. 07/989,098, entitled TRANS-URETHRAL RESECTION DEVICE, filed Dec. 11, 1992.

BACKGROUND OF THE INVENTION

1. Field of the Invention

The present invention relates to surgical probes which provide direct visualization for the surgeon at the distal end of the probe, and more particularly to such probes used for laser surgery to treat conditions such as benign prostate hyperplasia (BPH).

2. Description of the Related Art

With the advances in direct visualization techniques involving flexible, small diameter optical scopes that can be placed in a catheter, a surgeon is able to view a region being treated at the end of the catheter directly with the scope. However, when a direct visualization catheter is placed into a crowded region of the body, such as a hollow vessel, or a region between two organs which normally press together, the view through the scope may be obscured by tissue pressing on the scope.

There has been significant work in the area of direct visualization scopes using balloons to clear blood from the region of the tip of the scope to improve visualization. See Okada, et al., *Balloon Cystoscopy with Neodymium:YAG Laser*, THE JOURNAL OF UROLOGY, Vol. 148, 285-288, August 1992; Fujisawa, et al., Obtain Article. However, these designs have met limited success because of the difficulty in controlling the amount of laser radiation delivered through the balloon, and of preventing the radiation or effects caused by the radiation such as heat of the surrounding tissue from damaging or rupturing the balloon.

Other balloon type catheters have been used without direct visualization for a variety of treatments, including esophageal treatments as described in Panjehpour, et al., *Centering Balloon to Improve Esophageal Photodynamic Therapy*, LASERS IN SURGERY AND MEDICINE, 12:631-638 (1992). See also U.S. Pat. No. 4,998,930, to Lundahl, entitled INTRACAVITY LASER PHOTOTHERAPY DEVICE.

The results of such prior art systems have been mixed. Thus, there is a need for a direct visualization surgical probe mechanism which overcomes the difficulties encountered in the prior art, and which is suitable for use with delivery of laser radiation in controlled dosages.

One procedure in particular where such a probe is important is the treatment of Benign Prostate Hyperplasia (BPH). Generally, there are several ways to treat BPH. One type of treatment is trans-urethral incision of the prostate (TUIP) wherein a trans-urethral surgical instrument is inserted into the urethra to position an incisor adjacent the prostate gland. Once in position, an incision is made in the prostate into swollen tissue and reduce the amount of pressure the swollen gland exerts on the urethra. Other treatments for BPH include the use of drugs, or microwave hyperthermia.

A prevalent treatment in use today is trans-urethral resection of the prostate (TURP) wherein typically electro-cautery is used to remove swollen prostate tissue. Although many TURP techniques have developed, one current technique utilizes a laser probe, inserted into the urethra to direct laser energy onto selected portions of the enlarged gland, thereby creating coagulation necrosis of the target tissue, with the destroyed tissue sloughing off over time in tiny particles. The dead tissue particles are then passed out through the urethra upon urination.

One device for performing TURP in such manner is the Intra-Sonix TULIP System, manufactured by Intra-Sonix, Inc. of Burlington, Massachusetts. The Intra-Sonix TULIP device features a trans-urethral probe which is equipped with a single use balloon which is expandable at the distal tip of the probe. The distal end of the probe is inserted into the urethra and positioned adjacent the prostate, using a miniaturized ultrasound transducer and ultrasound imaging system. Once in place, the sleeve is expanded by pressurized sterile water and laser energy from a continuous wave Nd:YAG laser (1064 nm) of about 40 w of power is directed in a "side firing" manner onto the prostate.

Use of the pressurized sleeve or "balloon" at the tip of the probe provides both compression of the tissue adjacent the probe tip and a nominally constant distance between the probe tip and the tissue. Compression of the tissue allows deeper penetration of the laser energy into the tissue. A constant distance between the probe tip and the tissue is desired to ensure predictable energy distribution into the tissue.

However, the TULIP system is somewhat limited to the one particular use, i.e., TURP, since the system is designed to be used with its protective sleeve in all applications. Also, the TULIP system is quite expensive, requiring not only a laser, but also complex ultrasonic positioning mechanisms.

Another product recently announced is the Trimedyne "Lateralase" (also known as the "Eurolase"), by Trimedyne Corporation of Irvine, California. This device utilizes a catheter with a laser fiber designed to laterally direct laser energy to the affected area. Again, the Lateralase is designed to be inserted into the urethra and, once positioned adjacent to the prostate, to direct laser energy to a selected area of the prostate gland. The Lateralase laser probe is positioned visually by means of an endoscope, having an axial eyepiece aligned along the same axis defined by the length of the trans-urethral probe. The endoscope provides the surgeon with the most accurate representation of the effects of the laser on the areas of the prostate to which it is directed. However, the view may be obscured by swollen tissue and the like in the urethra.

In addition, the endoscope requires optical fibers coincident with the probe tip to provide light and viewing channels to the eyepiece. With the axial eyepiece being in line with the rigid trans-urethral cannula, placement of these fibers in the cannula in conjunction with the optical fiber for transmitting laser energy further complicates the structure of the surgical instrument.

Further, when using a flexible sheath and an optical fiber which is rotatable in the transverse plane, as in the TULIP system, it is desirable to have energy directed from the probe tip at a constant distance to the gland tissue over the entire rotation path to ensure uniformity in the amount of energy reaching the selected area. To ensure such equidistant length, the optical fiber for the laser in the TULIP system is centered with respect to the circumference of the sheath. Even centering the fiber does not ensure equidistance when the fiber tip is extended significantly beyond the tip of the probe due to possible flexing of the balloon relative to the probe or slight sagging of the fiber tip.

Another consideration in TURP systems is the temperature of the operating site. In particular, the heat generated by the laser incident on the tissue can cause the tissue to char, making it difficult to control the amount of tissue destroyed. Thus, it is desirable to control the temperature at the operating site such that coagulation necrosis of the tissue occurs at a rate which can be controlled by the surgeon.

It is also desirable to provide a surgical instrument utilizing a distension element, such as a balloon, to compress the tissue adjacent the energy delivery point and to tamponade superficial bleeding from the surface of the tissue. It is further desirable to ensure the distance between the energy delivery point and the tissue is constant when the balloon is distended and where the energy delivery point is rotatable in the transverse plane. It is also advantageous to provide such an instrument wherein an endoscope is utilized to view the surgical area, thereby yielding the most accurate representation of the surgical area to the surgeon. It is also desirable to provide such an instrument wherein the temperature at the operating site can be accurately controlled. Further, containment of the irrigation/cooling fluid may be critically important for some regions of the body such as the brain or blood vessels.

SUMMARY OF THE INVENTION

The present invention provides a surgical probe for use in a hollow vessel or other confined region of the body which comprises a multi-lumen catheter having a transparent, non-compliant balloon coupled to the distal end, such that the balloon has a known shape when inflated against the pressure of surrounding tissue. A direct visualization scope is provided in a first lumen of the multi-lumen catheter providing direct visualization into the hollow vessel through the non-compliant balloon. An adapter is coupled to a second lumen of the multi-lumen catheter near the proximal end to supply a transparent fluid through the second lumen to inflate the balloon to the predefined shape. In this aspect, the balloon operates to clear the scope tip by pressing tissue of the hollow vessel out of the way of the end of the scope and to provide a viewing region of a fixed shape. This provides the user of the device a consistent, clear view of the tissue on the walls of the hollow vessel that is unavailable in the prior art.

In another aspect of the present invention, a fiber optic is provided in a third lumen of the multi-lumen catheter to deliver light energy to the hollow vessel through the non-compliant balloon, which may be configured with a cylindrical section or other desired shape. Within the balloon, a mechanism is provided for positioning the light emitting tip of the fiber optic within the balloon to establish a known propagation distance to the surface of the balloon in the cylindrical section for the light energy emitted from the light emitting tip. This mechanism includes in one aspect a sheath that extends from the distal end of the catheter to the distal end of the balloon along the axis of the cylindrical section. The light emitting tip of the fiber optic slides within the sheath. At the proximal end of the catheter, a device is provided coupled to the fiber optic by which the surgeon is able to move the tip of the fiber within the sheath, both axially along the sheath, and rotationally.

Further, cooling fluid for the fiber optic tip is provided through the sheath into the balloon and is withdrawn through a lumen in the catheter to provide a flow of cooling fluid across the tip of the fiber optic to keep the fiber optic cool, and in contact with the surface of the balloon to cool the tissue being treated. Using a light emitting tip which laterally directs the beam from the fiber optic, the surgeon is able to axially position and rotate the fiber to irradiate the tissue in contact with the cylindrical region of the balloon with a uniform dosimetry unavailable in prior art devices.

The tool, as described above, is particularly suited to the treatment of prostate conditions. In this aspect, the balloon is positioned adjacent the prostate, such as trans-urethrally, and inflated to compress the prostate tissue. The fiber optic tip provided laterally directs the beam into the cylindrical section of the balloon and irradiates the compressed tissue. By compressing the tissue, the effective depth of the irradiation is increased for a given application. Furthermore, the fluid inflating the balloon is cooled to below about 10° C., in order to increase the amount of laser energy that may be provided without charring the tissue. Direct visualization allows the surgeon to view the results of the radiation contemporaneously with applying the radiation. Also, the tool allows the surgeon to move the fiber within the balloon to treat a larger region of the prostate, with direct visual feedback of regions that have already been treated or have not been treated.

In another aspect, the invention may be characterized as a surgical tool having a unique combination of elements providing for an improved method for conducting trans-urethral resection of the prostate. In this aspect, the tool comprises: a first tube having a length, a proximal end and a distal end, the length defining an axis; a second tube having a proximal end and a distal end, secured essentially parallel to the first tube with the distal end of the second tube near the distal end of the first tube; a coupling for securing an energy delivery device, such as a fiber optic, to at least one of the first and second tubes and along the length thereof; a coupling for securing a dilation element at the distal end of the first and second tubes; a coupling for securing a source of pressurized fluid coupled to the first and second tubes; and a coupling for securing an optical viewing scope to the proximal end of the first and second tubes.

The optical viewing scope may comprise a cystoscope or endoscope, wherein the scope includes the off-axis eyepiece, a viewing channel optical fiber positioned in the second tube and extending to the distal end thereof, and at least one light channel optical fiber in the second tube extending to the distal end thereof. By using an off-axis optical viewing scope, the fiber optic element, or other energy delivery device, may enter the first and second tubes without being bent with respect thereto. A straight instrument channel allows for a more rigid energy delivery device. This enhances placement, is more durable, and increases accuracy.

In another aspect, circulating saline solution is provided to distend the dilation element, and may be used to control the temperature of the region adjacent the dilation element. Temperature control of the operating site yields a greater degree of control over tissue removal for the surgeon.

In a further aspect, a laser probe is provided in the second tube, the first tube has a circular cross-section, and the laser probe is off-set from the center of the circular cross-section. In this aspect, the dilation element comprises a balloon coupled to the distal end of the second tube wherein the balloon has an anterior portion having a circular cross-section, with the laser probe being concentric with respect thereto. The balloon shape is thus eccentric with respect to the circular cross-section of the tube, and the fiber optic elements for light and vision may be positioned in the second tube with the laser probe offset with respect to the central axis of the tube, simplifying assembly of the elements present in the second tube.

Accordingly, an improved surgical probe is provided which allows for direct visualization in hollow vessels or other crowded regions of the body based on the use of a non-compliant balloon over the end of the scope. Also, a fiber optic is incorporated with the scope and enclosed within the balloon. A positioning mechanism precisely controls the position of the tip of the fiber within the balloon and allows precise positioning by the surgeon during the procedure under direct visualization. The fluid used to inflate the balloon may also be used for the purpose of cooling the fiber optic and the tissue to be treated. Furthermore, the balloon is used to compress the tissue in the region being irradiated, not only to improve visualization, but to improve the penetration of the laser dosage. Thus, significant advantages are provided over prior art systems using the direct visualization laser probe as described herein.

Other aspects and advantages of the present invention can be seen upon review of the figures, the detailed description, and the claims which follow.

BRIEF DESCRIPTION OF THE FIGURES

FIG. 4 is a schematic view of a surgical probe for use in trans-urethral resection of the prostate according to the present invention.

FIG. 5 illustrates construction of the shaft of the probe illustrated in FIG. 4.

FIGS. 13A–13C illustrate an alternative handle mechanism for controlling the axial positioning of the fiber tip according to the present invention.

FIG. 14 illustrates another alternative handle mechanism for axially positioning the fiber tip in the probe of the present invention.

FIG. 15 illustrates yet another alternative handle mechanism for axially positioning the fiber tip in a probe of the present invention.

DESCRIPTION OF THE PREFERRED EMBODIMENTS

A variety of embodiments of the present invention are described with reference to FIGS. 3–23A/23B. For background, representative prior art systems are described with reference to FIGS. 1 and 2.

Figure 1:
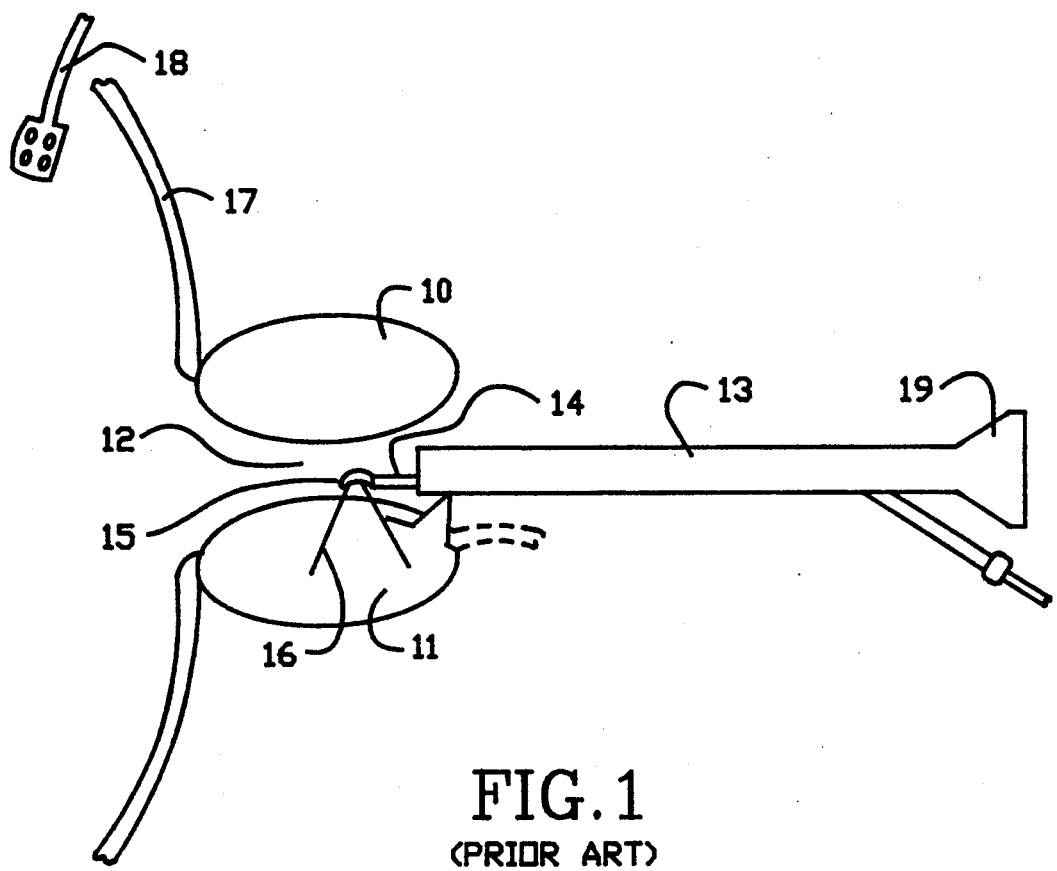
FIG. 1 illustrates a prior art surgical procedure used for trans-urethral resection of the prostate.

FIG. 1 illustrates a prior art technique for treating the BPH. The prostate has a first lobe 10 and a second lobe 11 which, in this cross-section view, is separated by the urethra 12. A catheter 13 is inserted into the urethra so that a fiber optic 14 may be positioned between the lobes 10, 11 of the prostate. The fiber optic 14 has a tip 15 for laterally directing the laser beam, generally 16, into the prostate to cause ablation of swollen prostate tissue.

The bladder neck 17 abuts the lobes 10, 11 of the prostate. With the fiber optic tip 15 positioned adjacent the prostate, laser energy is delivered to the prostate to cause ablation, and reduce the volume of the prostate tissue. During the treatment, a cooling fluid is supplied into the urethra through the catheter 13. This cooling fluid, for the most part, gathers in the bladder region. Thus, for longer procedures, a means for removing the fluid from the bladder is needed, such as a super-pubic drainage catheter 18. The catheter 13 also includes an optical viewing scope, generally represented by eyepiece 19, which allows the surgeon to view the treatment area visually. However, visualization is hampered by the swollen prostate tissue. Furthermore, it is difficult to precisely position the tip 15 of the fiber within the urethra with the probe of FIG. 1.

Figure 2:
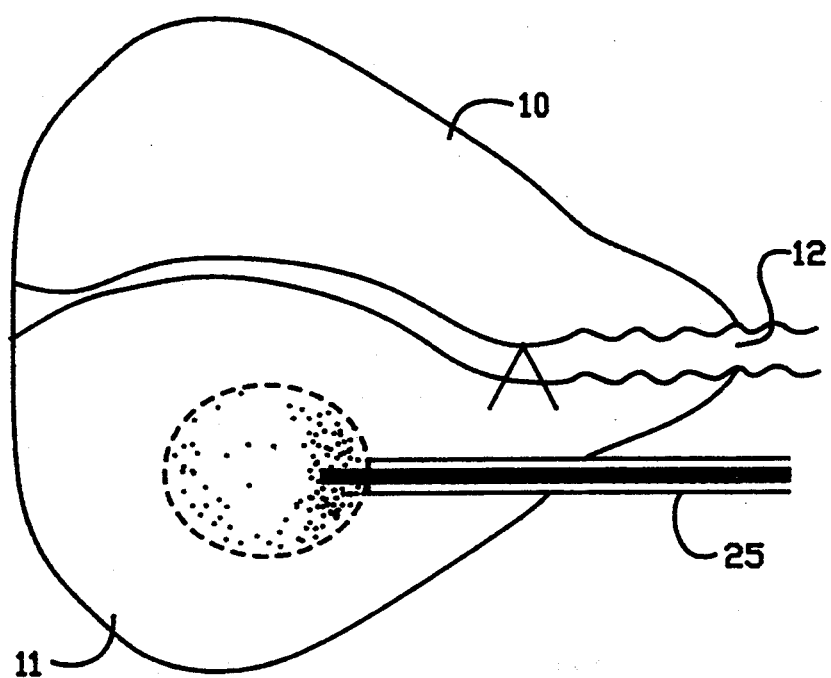
FIG. 2 illustrates a prior art procedure using laser energy to treat enlarged prostate.

FIG. 2 illustrates an alternative technique used in the prior art for treating the BPH. In particular, a laser probe 25 is interstitially placed within the lobe 11 of the prostate. Laser energy is delivered directly to the prostate tissue, which causes necrosis and eventual reduction in size of the prostate. This technique is also problematic because it is difficult to control the amount of tissue killed using the procedure, and to insure that it is all sloughed off.

Figure 3:
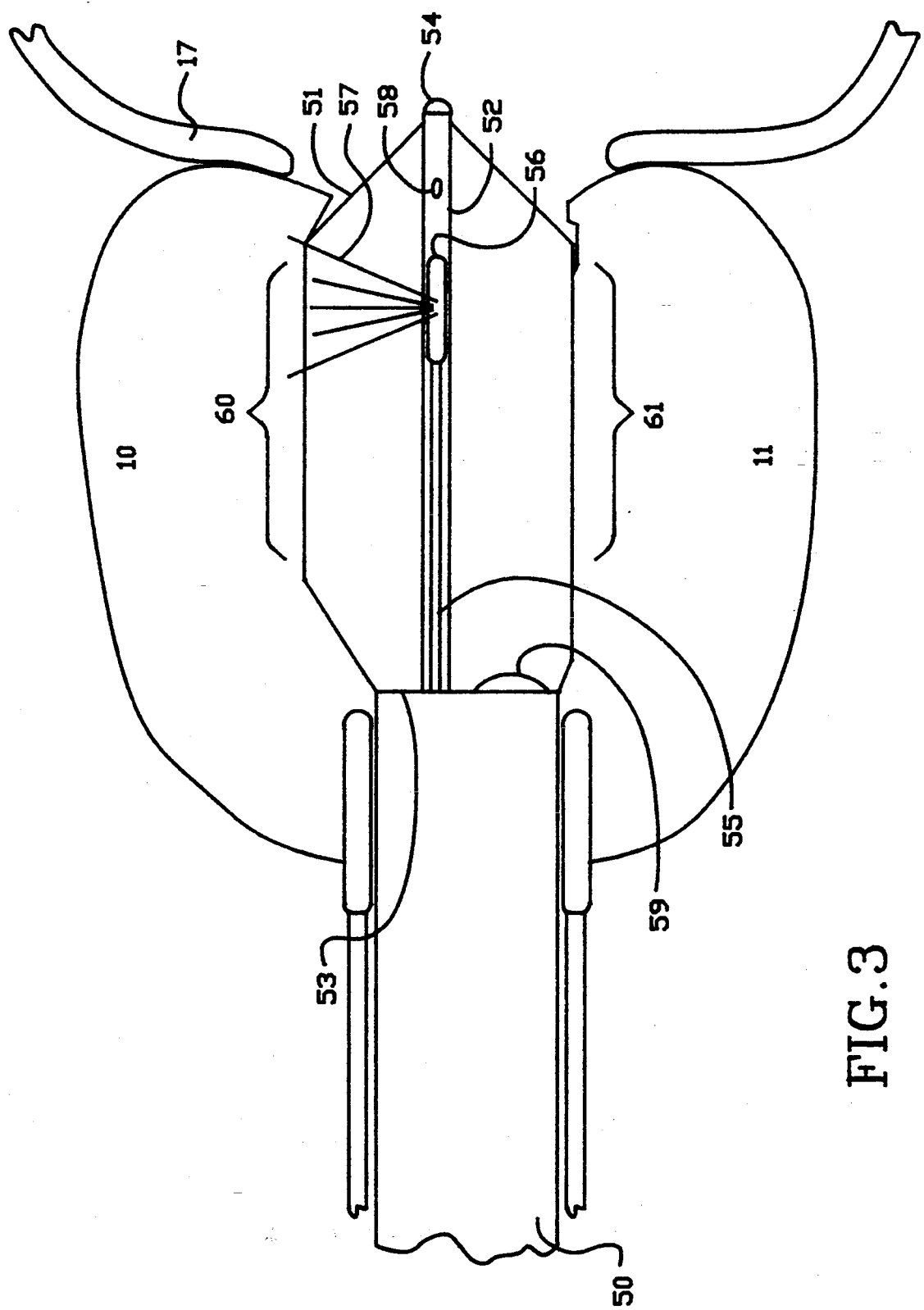
FIG. 3 illustrates the treatment of an enlarged prostate using the surgical probe of the present invention.

FIG. 3 illustrates application of the present invention for treatment of BPH. In particular, a probe, generally 50, is inserted through the urethra for positioning between the lobes 10 and 11 of the prostate. A balloon 51 coupled to the tip of the probe is inflated with saline solution. The balloon 51 is a non-compliant balloon so that when it is inflated, it compresses surrounding tissue as necessary to assume a known shape and volume. Within the balloon 51, a guide channel 52 extends from the end 53 of the catheter 50 to the tip 54 of the balloon 51. Within the guide channel 52, a fiber optic 55 is inserted with a tip 56 which causes lateral deflection of the laser beam along the path generally 57. A port 58 is opened in the channel 52 to allow fluid for inflation of the balloon to be passed from the channel 52 through the port 58 and into the balloon 51 to inflate it. A return flow path (not shown) is provided in the catheter 50 to allow circulation of fluid during the procedure. A viewing scope covered by a lens cap 59 is mounted within the catheter 50 to provide direct visualization within the balloon 51 for use during the treatment. The channel 52 allows manipulation of the fiber tip 56 by the surgeon both axially along the guide channel, and radially, so that the surgeon may direct the laser beam 55 as desired within the working range of the balloon 51.

The balloon, because of its predefined shape and non-compliant nature, in combination with the guide channel 52, ensure precise positioning of the fiber tip 55. Thus, the radiation density at the surface of the balloon in the region generally 60 and 61 is precisely controlled.

This technique has a number of advantages over prior art systems. In particular, the cooling fluid is contained by the balloon and the return flow passage, so that there is no leaking of fluid into the patient's body. The surgeon is able to directly visualize the treated region, through which he can determine by coloration and the like, the progress of the treatment. The surgeon has precise positioning control axially and radially for delivery of a precise dose of laser energy. Furthermore, by using a chilled liquid to inflate the balloon 51, the temperature of tissue of the prostate lobes 10, 11 can be controlled, so that less charring of the tissue occurs during the treatment. The use of the guide channel for a coolant flow path insures that cooling fluid flows across the tip 56 of the fiber optic 55, to insure effective cooling of the tip, and thereby prolonging the life of the tip 56. Finally, by using a non-compliant balloon, that can be inflated with significant pressure, the lobes 10, 11 of the prostate are compressed. As has been established, the compression improves the reach of the treatment. Using this direct visualization probe, the tissue on the walls of the urethra against the balloon can be viewed clearly and consistently by the surgeon.

Figure 19:
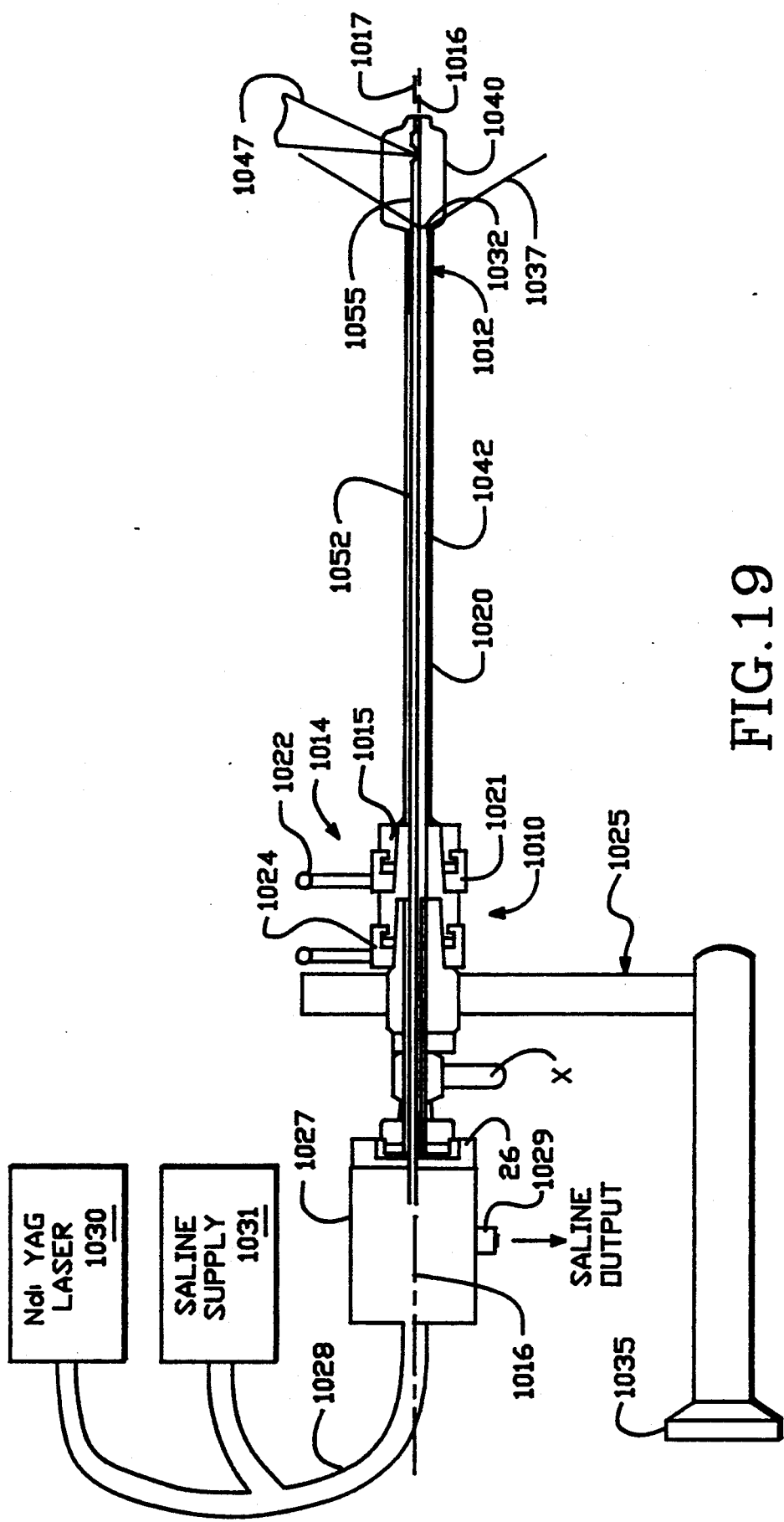
FIG. 19 illustrates a surgical tool for treatment of an abnormally enlarged prostate gland.
Figure 20:
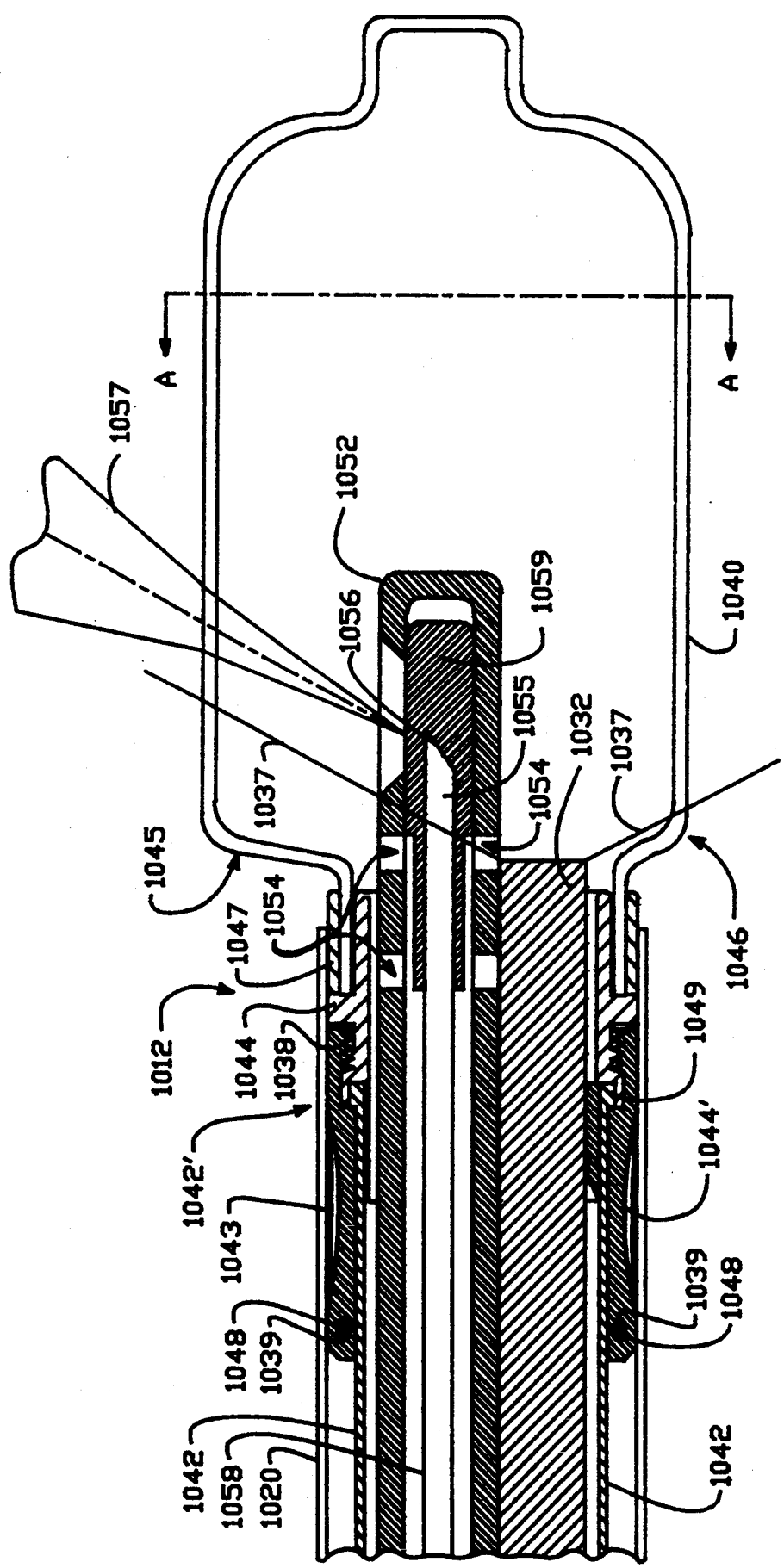
FIGS. 20 and 21 are enlarged views of the distal end of the surgical tool shown in FIG. 19 with the probe tip in the extended and retracted positions, respectively, for an embodiment without a mechanism for positioning the fiber tip within the balloon.

FIG. 4 provides a perspective of the surgical tool, including the catheter, according to the present invention, which is placed in a hollow vessel using a technique as described below with reference to FIG. 19. The tool includes a shaft 100 coupled to a handle 101. The shaft 100 is an extruded plastic member having a plurality of lumens, including a scope lumen 102, an inflation lumen 103, and a deflation lumen 104. Further, a lumen 106 for the fiber optic is provided. At the proximal end, generally 107 of the shaft 100, a torsional knob 108 is mounted, by which the surgeon is capable of axially turning the fiber optic so that the laser beam, generally 109, rotates. Coupled to the torsional knob 108 is a mandrel 130 which translates motion of the torsional knob 108 to twisting of the tip of the fiber 55 using techniques known in the art. A balloon is secured at the distal end of the probe, using a structure such as illustrated in FIG. 20 below.

According to this embodiment, cooling fluid is applied both along the fiber optic lumen 106 and the inflation lumen 103. The inner guide channel 52 extends from the fiber lumen 106 to the tip 54 of the balloon. It is glued or otherwise secured to the tip 54 of the balloon 51 to provide a smooth, durable tip. A coolant port 58 is included in the inner guide channel 52. The fiber 55 lies within the inner guide channel 52 for precise positioning as described above. The laser beam exits the fiber tip in a precise pattern, generally represented by region 109, that can be well predicted at the surface of the balloon 51.

On the proximal end 107 of the probe, handle 101 is attached. The handle 101 includes a lever 110 for controlling axial positioning of the fiber 55. Also, a circulation toggle 111 may be included for turning on and off fluid circulation into and out of the balloon. A viewing scope 112 is inserted into the handle 101, positioning a viewing lens at the distal end, generally 113, of the shaft 100. The surgeon is capable of seeing inside the balloon 51 through the scope 112. Light cord attachment 112A on scope 112 provides an input for illuminating the field of view of the scope 112. A tubing jacket 114 extends out of the handle 101 to coupling 115. The coupling 115 illustrates the fiber tubing 116 which carries the optical fiber to a laser connector 117. Also, a drip chamber 118A coupled to a bag of saline solution for inflating the balloon 51 is coupled through tubing 118, valve 119, and into tube 120 through coupling 115 into the inflation lumen 103 and fiber lumen 106. Deflation tubing 121 exits the coupling 115 and through valve 122 is coupled to a Luer fitting 123 for proper disposal of the exhaust fluid.

As illustrated in FIG. 5, the shaft 150 is basically an extruded plastic member 150 having a scope lumen 102, an inflation lumen 103, a deflation lumen 104, and a fiber lumen 106. Other materials may be used as suits the needs of a particular design, such as surgical grade steel, which may be sterilized and reused.

Figure 6:
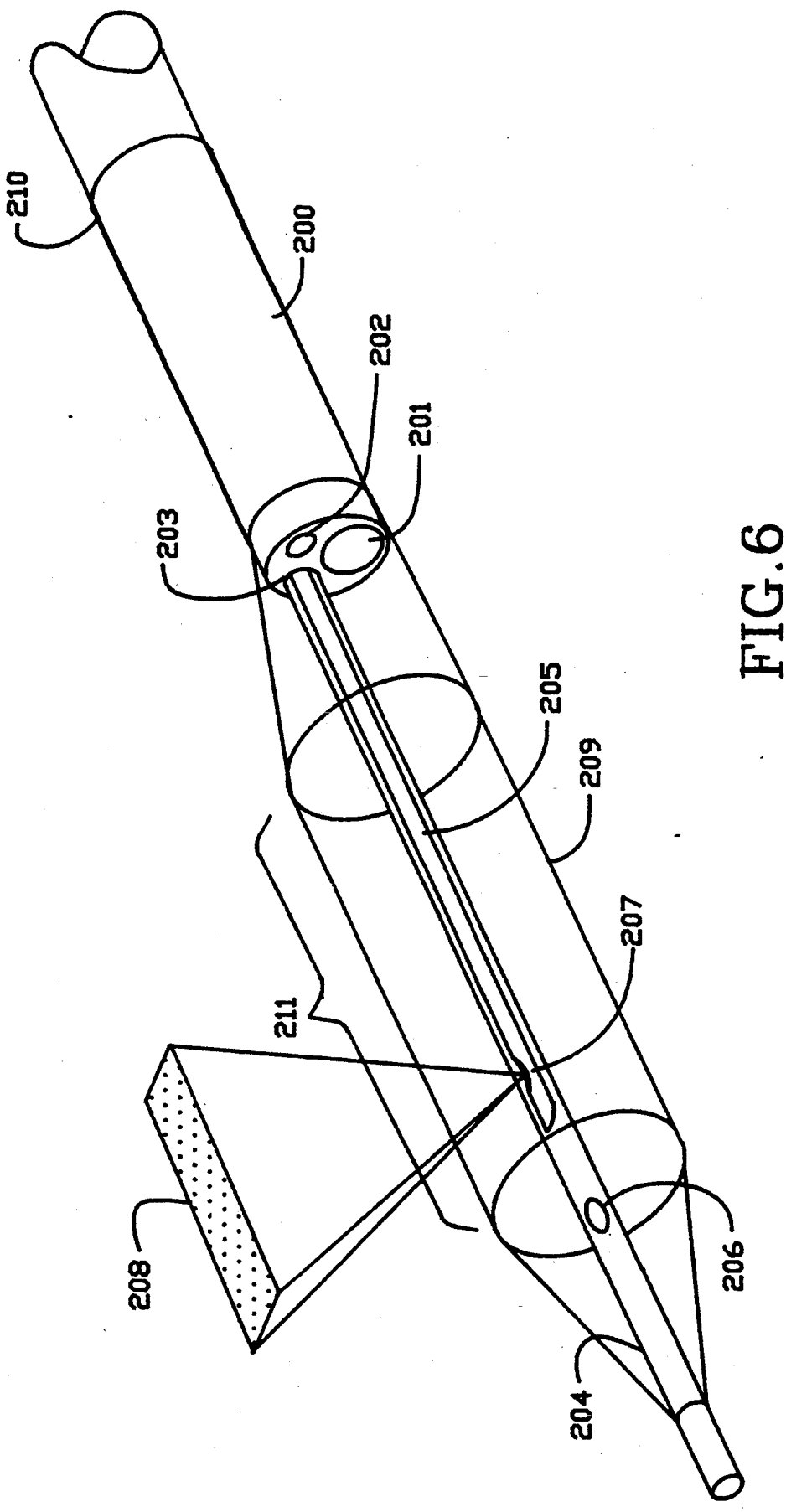
FIG. 6 is an enlarged view of the balloon tip of the probe shown in FIG. 4.

FIG. 6 illustrates an alternative view of the probe tip. In this embodiment, the shaft 200 has three lumens, including a scope lumen 201, a deflation lumen 202, and a fiber lumen, generally 203. Within the fiber lumen, the inner guide channel 204, which provides a channel for the fiber optic 205, is secured. The inner guide channel 204 has a fluid port 206. The tip of the fiber 205 has a laterally directing mechanism, generally 207, which directs the laser beam in a pattern, such as illustrated generally at 208. The balloon 209 is a non-compliant balloon which extends over the shaft 200 to region 210 to provide a secure fit, and to seal the balloon against leaking fluid during inflation. In order to inflate the balloon, fluid is passed through the inner member 204 out port 206 and into the balloon. A return flow path is provided through the deflation lumen 202.

The non-compliant balloon 209 shown in FIG. 6 has an asymmetrical design providing a cylindrical region, generally 211, having an axis along which the fiber 205 lies, where the fiber lumen 203 is not on the center axis of the probe shaft. Non-compliant materials have sufficient rigidity that the balloon maintains its shape in desired environments (vessels, tissues, organs, cavities) with known internal pressure and under external pressure applied by environment. This design is suited particularly for treatment of BPH. The length of the balloon can vary from 1 to 3 centimeters. The diameter is selected as appropriate to the size of the patient. The material of the balloon in the preferred system is polyethylene teraphaleate (PET). Other non-compliant transparent materials, such as materials based on nylon or polyethylene or other polyolefins or ionomers may be used as suits the needs of a particular design. Some transparent elastomers may also be used, such as neoprene, sanoprene, polyurethane, and silicone.

In the preferred system, the balloon is inflated using a cooled fluid or temperature controlled fluid driven by an endoflater with up to 300psi of pressure. Alternative systems may use gas, such as air, as the fluid to inflate the balloon and be driven to the compressor to the desired pressure. The cooling characteristics of a liquid may be superior to gas in many applications.

In the embodiments described here, the balloon is shaped in a manner suitable for trans-urethral resection of the prostate. Other shapes may be designed, and other positioning mechanisms adapted to those other shapes, as are suited to a specific confined body region or vessel and a specific treatment.

As can be seen in FIG. 6, the inner member 204 precisely positions the fiber tip 207 along the axis of the cylindrical region of the balloon 209, and allows for rotation of the tip 207 through 360°.

Thus, the surgeon can be assured that for the same amount of input energy and time of illumination, a particular region on the surface of the balloon 209 will receive the same amount of radiation as other portions. This allows the surgeon greater control over the surgical procedure in general. Also, using the scope 201, the surgeon can directly visualize the results of the illumination, and keep track of the progress of the procedure. Thus, discoloration caused by the necrosis of the tissue can be monitored to see regions which have been treated and which have not, and by differences in the color of treated regions, an estimate of the effect of the treatment can be gauged. This direct feedback can be critical for successful surgical operations. Also, the presence of a non-compliant balloon 209 which has a known shape, and smooth clear sides enhances the visualization available to the surgeon. In fact, the surgeon can see much better in this type of procedure using a non-compliant balloon over the scope 201, than without the balloon.

Figure 7:
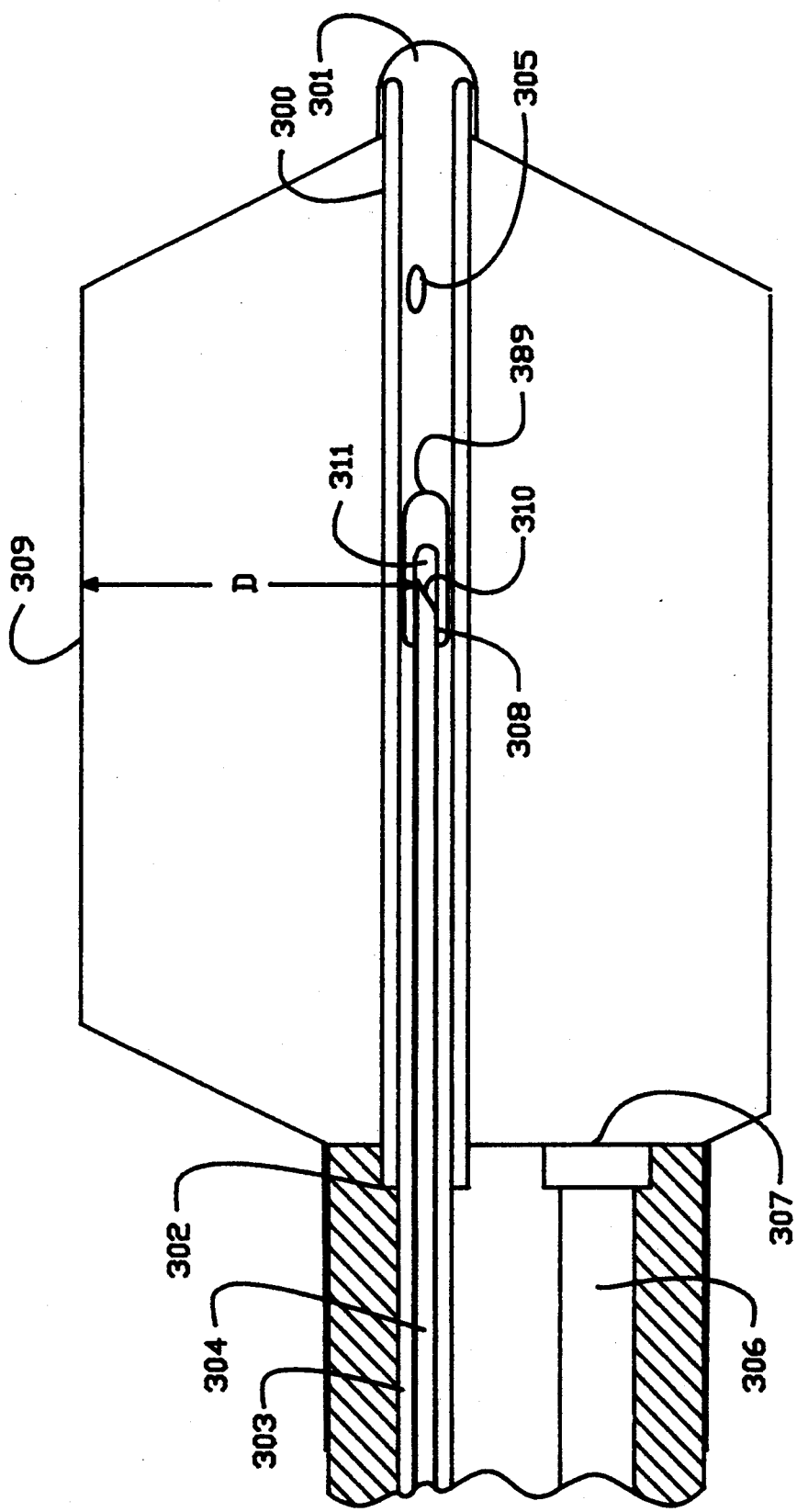
FIG. 7 is a cross-sectional view illustrating construction of the balloon and fiber positioning mechanism in a probe according to the present invention.

FIG. 7 is a cross-sectional view of the balloon structure according to the present invention. As can be seen, the inner member, generally 300 in FIG. 7, comprises a tube of transparent thermal plastic which is plugged using medical grade adhesive, or heat seal, at the tip 301. Alternative systems may use a urethane or silicone cap to soften the tip to decrease the potential for injury. Materials other than transparent thermal plastic which are suitable for the tube 300 include quartz or silica tubes, however, such materials may be more prone to breakage. The tube 300 is secured within recess 302 formed at the end of the fiber lumen 303, using adhesives. The fiber 304 is passed into the tube 300 through the lumen 303. Also, cooling fluid is allowed to pass through the lumen 303 and out port 305 to inflate the balloon.

The scope lumen 306 is covered by a transparent lens cap 307 to seal the scope 306 from the relatively high pressure fluid within the balloon when inflated.

As can be seen in FIG. 7, the distance D from tip 308 of the fiber 304 to the surface 309 of the balloon is uniform through a working region of the balloon structure. Also, the distance D is equal on each side of the fiber tip 308. Thus, as the fiber tip is rotated through essentially a 360° turn, the distance from the fiber tip 308 to the surface 309 of the balloon is constant. In this embodiment, a tip cover 389 is secured over the reflecting surface 310 of the fiber 304, to enclose air in region 311. This contains a selected medium in contact with surface 310 for control of the critical angle for internal reflection. In alternative systems, no cover will be needed. For instance, if the guide channel 300 is air filled, no cover 309 may be required.

Figure 8:
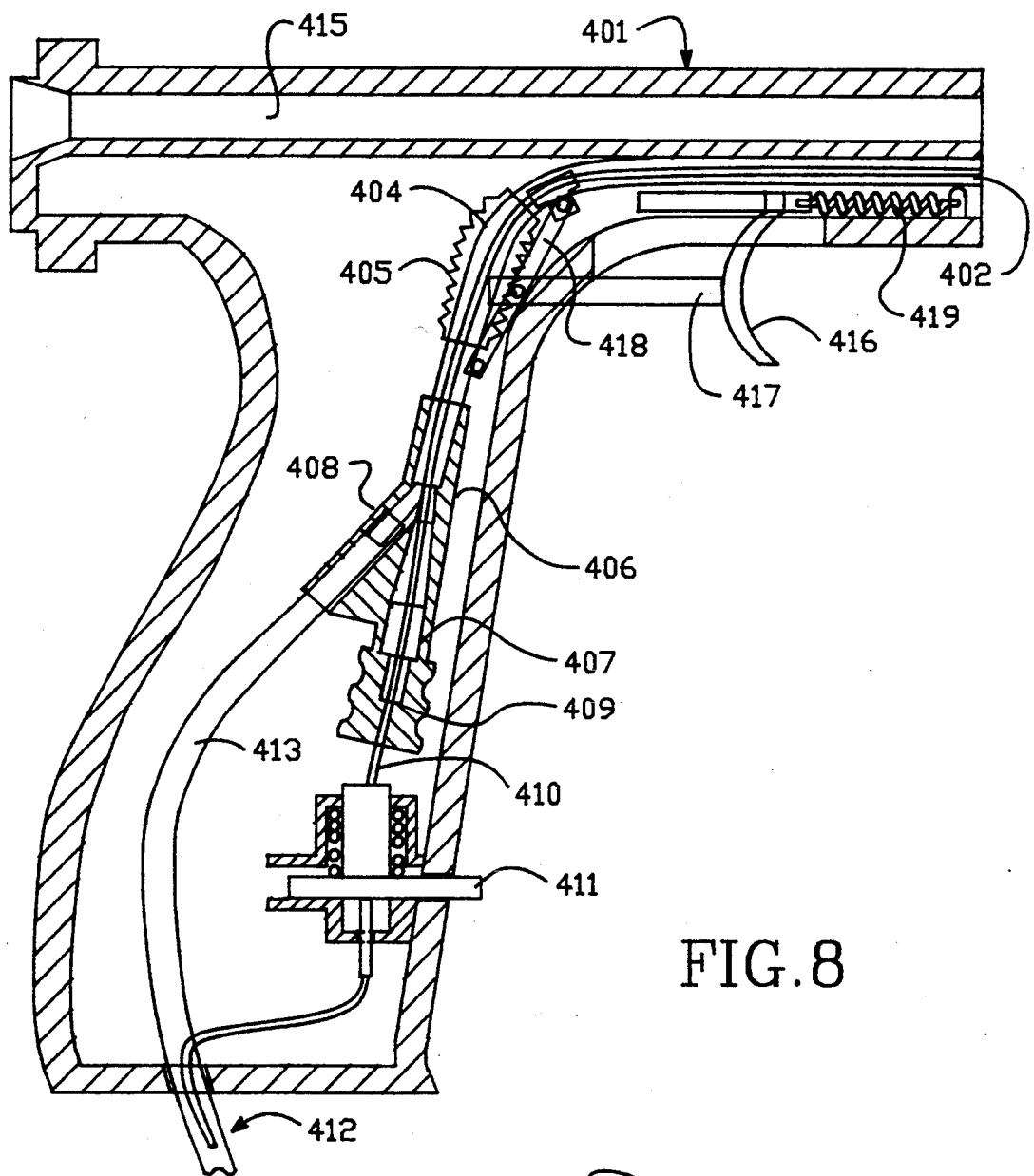
FIG. 8 is a schematic representation of a handle including the mechanism for providing axial and rotational control of the tip of the fiber optic in a probe according to the present invention.

FIG. 8 schematically illustrates a handle, including a mechanism for controlling the positioning of the fiber tip 308. In this system, the shaft (not shown) of the probe is coupled to a handle 401. The fiber lumen 402 is coupled to tubing 404. The tubing 404 includes a bellows type flexible region 405, and a rigid coupling member 406, which has a first branch 407 and a second branch 408. The first branch 407 is stopped by a rubber stopper 409 which has a hole to receive the fiber 410. The stopper 409 seals the fluid within the region but allows rotation of the fiber 410 as necessary. The fiber 410 is then bonded to a wheel 411, and passes out of the handle 401 into a tubing bundle 412. The second branch 408 of the tube 406 is coupled to tubing 413 which passes into the tubing bundle 412 for the purpose of supplying inflation fluid. The return flow for the fluid is provided through separate tube (not shown) which is coupled to the deflation lumen in the shaft 400 by mechanism not shown. The scope lumen 415 receives the scope for use by the surgeon.

In order to control the position of the fiber tip 308 of FIG. 7, this mechanism provides a wheel 411 to rotate the tip. By rotating the fiber at point 411, the tip essentially rotates the same amount, due to the rigid glass structure of the fiber. Thus, for a length of a probe 400 of about 10 inches, a direct substantially one-to-one rotation of the tip can be expected per rotation of the wheel.

For axial movement of the fiber, the flexible bellows region 405 of the tubing is relied upon. A trigger mechanism 416 is used to push on the bellows region 405 of the tubing. Because the fiber is secured at the wheel 411, the tip 308 of the fiber moves axially through the tube 300 in response to depressing on the trigger 416. Thus, the trigger 416 is coupled to a shaft 17 and lever 418. Lever 418 pushes against the bellows 05 or flexible region of the tubing. The mechanism is spring loaded, as illustrated schematically by spring 419, so that when the surgeon releases the trigger 416, the fiber tip moves back into its extended position. Also, a locking mechanism, not shown, may be used so that the surgeon can lock the position of the trigger 416 in a depressed position.

Figure 9:
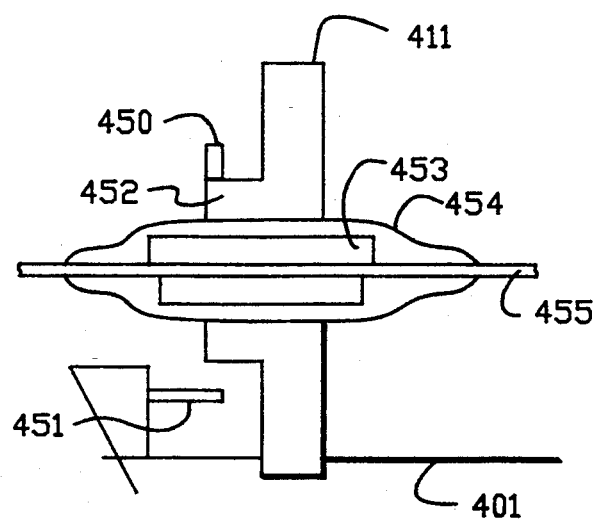
FIG. 9 illustrates a technique for bonding a radial positioning wheel to an optical fiber for use in a handle as illustrated in FIG. 8.

FIG. 9 schematically illustrates the region of the handle 401 including the wheel 411. The wheel 411 is designed so that it has a maximum rotation distance to prevent stressing the fiber with too much twisting. The wheel 411 includes the dial pin 450 on segment 452 of the wheel 411. A post 451 is mounted on the handle 401 so as to block the motion of the dial pin 450 after 180° rotation of the wheel 411. This allows rotation of the wheel 411 through a 360° path.

FIG. 9 also illustrates the mechanism for securing the fiber to the wheel 411. According to this embodiment, the fiber is first bonded to a heat shrink tube 453 which forms a secure bond with the fiber. Next, a second layer of heat shrink tubing 454 is applied over the first layer of heat shrink tubing 453. The wheel 411 is then bonded to the second layer of heat shrink tubing 454 using adhesive or other techniques known in the art. This bonding technique provides a sturdy, secure bond to the fiber 455, and distributes the load of the wheel 451 on the fiber 455 so as to improve the durability of the device.

Figure 10:
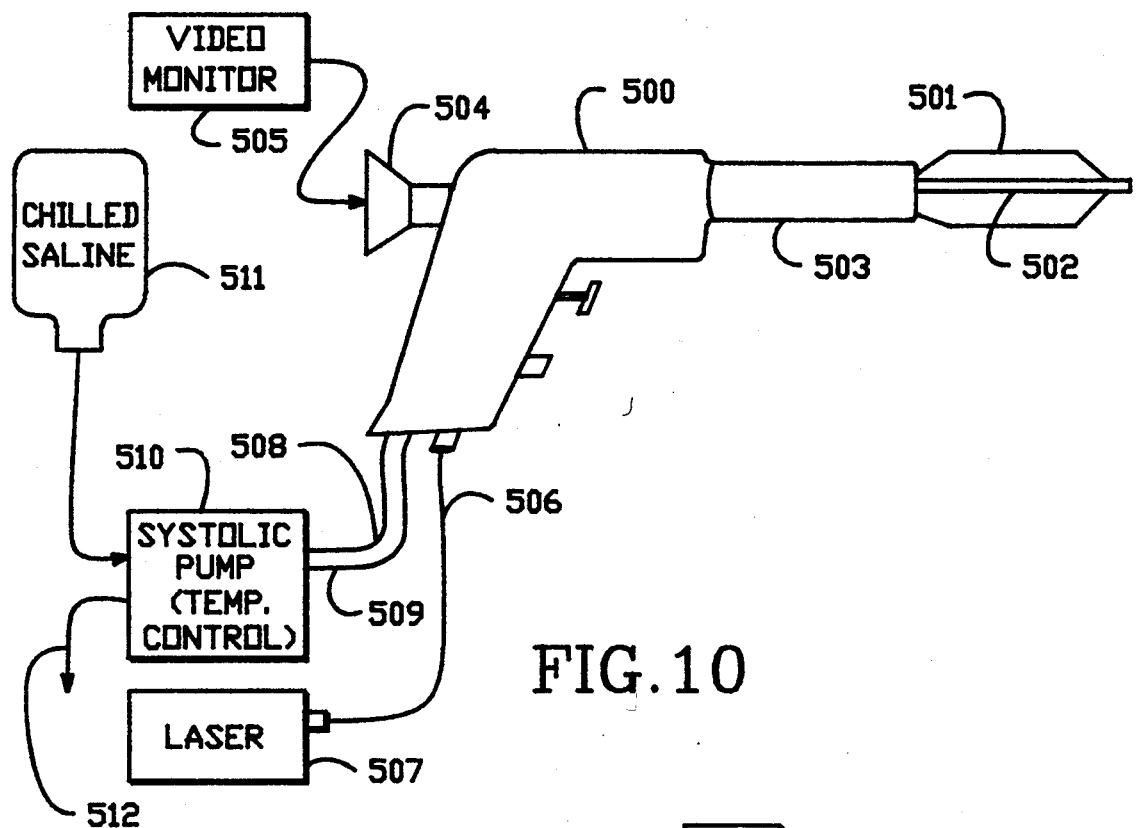
FIG. 10 is a schematic view of a laser probe including the supporting devices such as a pump, video monitor, and laser, according to the present invention.

FIG. 10 provides a schematic illustration of a system implementing the present invention. Thus, the system includes a surgical probe, generally 500, which includes the non-compliant balloon 501 and fiber guiding mechanism 502 as described above. The probe 500 also includes a shaft or catheter 503 for delivering the fluid, laser energy, and scope remotely into the balloon 501. The scope 504 can be used to visually position the balloon directly by looking into an eyepiece, and then a camera coupled to the eyepiece 504 for display of the direct visualization on a video monitor 505. Also, the fiber optic is coupled across fiber 506 to a laser 507 such as the Neodymium YAG:KTP laser system manufactured by Laserscope Surgical Systems, of San Jose, California.

The fluid path is provided through tube 508 for inflation of the balloon and tube 509 for deflation. In the preferred system, these tubes are coupled to a systolic pump 510, which receives fluid from a drip bag 511, filled with chilled saline solution. Return flow fluid is disposed across path 512 as known in the art. Systolic pump 510 may also include a heat exchanger or other mechanism for controlling precisely the temperature of the fluid being delivered into the balloon 501. For instance, in the preferred system, temperature control may be provided over a range of 3°–25° C. for BPH treatments using the probe of the present invention. Preferably, the temperature of the saline is delivered between 3° C. and 5° C., or under 10° C., to maintain the temperature of the treated tissue low. This cools the urethral surface sufficiently that a greater amount of energy is necessary before charting of the tissue occurs.

Figure 11:
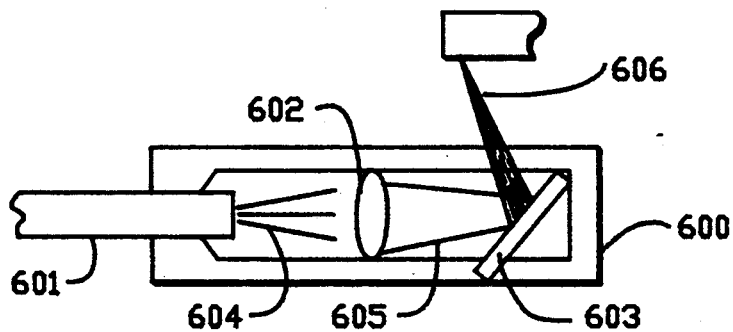
FIG. 11 illustrates an alternative embodiment of a fiber tip used for cutting tissue which may be used with the probe of the present invention.

FIG. 11 illustrates alternative fiber tip embodiments, so that the probe of the present invention can be used for other treatment techniques. For instance, as shown in FIG. 11, the fiber tip may include a capsule 600 to which the fiber 601 is connected. A lens 602 and a reflector 603 are aligned within the capsule 600 for the desired optical effect. The laser energy exits the fiber generally at 604 and is focused by lens 602, generally as shown along path 605. Reflector 603 reflects the beam along path 606 to a focal point F. Using the non-compliant balloon structure of the present invention, the fiber tip capsule 600 can be precisely positioned within tissue, so that the focal point F is at the desired position relative to the balloon surface.

Figure 12:
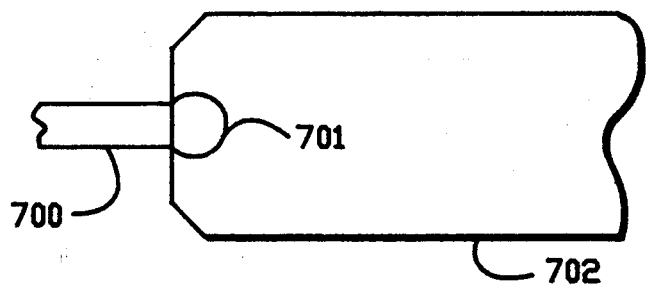
FIG. 12 illustrates an alternative embodiment for a fiber tip which may be used for delivering diffuse radiation in a probe according to the present invention.

An alternative system is shown in FIG. 12. In this embodiment, the fiber 700 is coupled to a spherical orb 701 to illuminate the balloon region uniformly. Thus, because the balloon 702 has surfaces with a known position relative to the spherical orb 701, the symmetry delivered by such system can be readily predicted. The diffuse beam generated by the spherical orb tip might be used in such procedures as photodynamic therapy or angioplasty.

FIGS. 13A–13C illustrate an alternative technique for controlling axial position of a fiber tip in a probe according to the present invention. FIG. 13A, a cross-section view of the handle 800 is provided. The fiber 801 extends along the path extending up the handle 800 and into the shaft, generally 802, of the probe. A post 803 is bonded to the fiber near the shaft 802. By moving the post 803, as indicated by arrows 804, the axial positioning of the fiber tip is controlled.

FIG. 13B illustrates a side view of the handle 800. The handle 800 includes notches 805 and 806. In order to move the fiber tip, the surgeon moves the post 803 upward out of the notch 805, and axially along the handle 800 to notch 806. This provides a precise positioning mechanism with two positions that can be used by the surgeon doing the procedure.

FIG. 13C is a back view of the handle 800 illustrating the post 803 extending laterally out of the side of the handle 800.

FIG. 14 illustrates an alternative technique for controlling the positioning of the fiber. In this mechanism, the handle 800 includes a lever 810 coupled to a fulcrum 811. A trigger 812 is coupled to the lever. By moving the trigger 812, the lever moves from a first position, generally 813, to a second position 814, and to a third position 815. By coupling the fiber to the tip of the lever 810, the axial positioning of the fiber can be controlled.

FIG. 15 illustrates yet an alternative embodiment using a rack and pinion technique. Thus, the fiber 801 extends through handle 800. It is secured to post 815 at point 816. The post 815 is coupled to a pinion gear 817. A rack gear 818 is coupled to a trigger 819. By depressing the trigger 819, the rack gear 811 turns the pinion gear 817, and moves the lever 815 to control the axial positioning of the fiber.

Alternative systems may provide a single, fixed axial position for the fiber tip, which is suited to the particular non-compliant balloon shape and procedure in which it is to be used, while allowing rotation of the fiber tip in the fixed axial position.

Figure 16A:
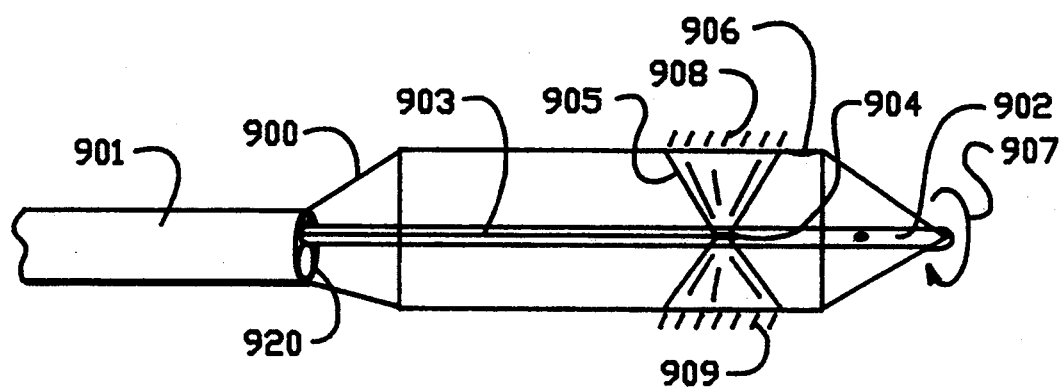
FIGS. 16A–16C illustrate operation of the positioning mechanisms for use with a probe according to the present invention.
Figure 16B:
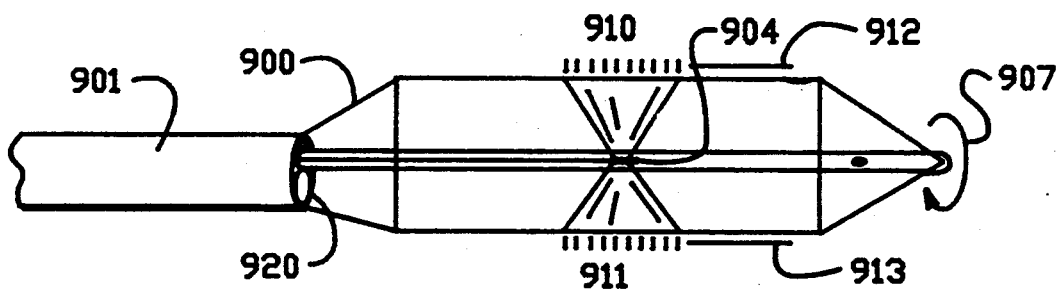
Figure 16C:
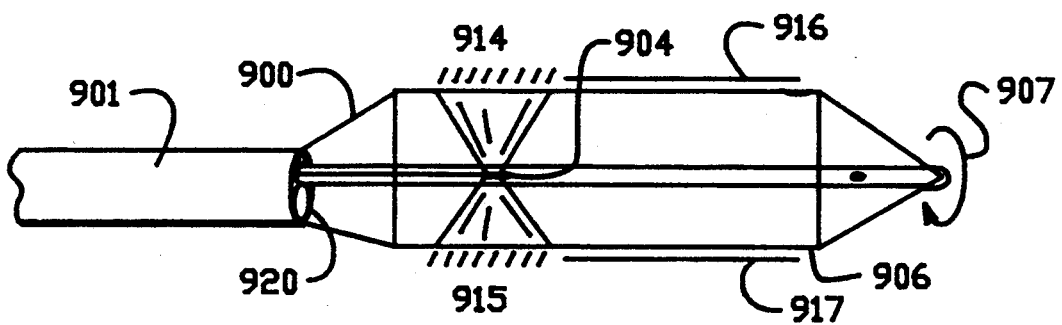

FIGS. 16A–16C illustrate the use of the positioning mechanism in a surgical probe according to the present invention. As can be seen in FIG. 16A, a balloon 900 coupled to a catheter 901 is illustrated. An inner member 902 operating as a guide for optical fiber 903 is mounted in the system as described above. The fiber tip laterally directs the laser beam in a pattern, e.g., 905, to the surface 906 of the balloon 900. By rotating the fiber 903 as indicated by arrow 907, a region of the tissue to be treated which surrounds the balloon 900 is irradiated. This region is illustrated by hatches 908 and 909. It would be understood that these regions may encircle the balloon due to the rotation of the fiber around 360°. Because the balloon 900 has a non-compliant cylindrical shape in this region, an essentially uniform dosage can be delivered to the tissue in regions 908, 909.

As illustrated in FIG. 16B, the surgeon may then reposition the fiber tip 904, and rotate the fiber as illustrated by arrow 907. This irradiates regions 910 and 911 with a dosage essentially identical to the regions 908 and 909 illustrated in FIG. 6A. Also, through the direct visualization, the surgeon may see discoloration as indicated by lines 912 and 913 of the tissue which had been treated by irradiating regions 908 and 909.

After irradiating the regions 910, 911, the surgeon may then reposition the fiber tip 904 as illustrated in FIG. 16C and irradiate the regions 914 and 915 by rotating the fiber as illustrated by arrow 907. The treated area visible through the scope 920 now includes the region treated during irradiation of regions 910 and 911 as well as the regions irradiated during treatment of regions 908 and 909 as indicated by lines 916 and 917. After treatment of the regions 914 and 915, the surgeon has irradiated a substantial region along the surface 906 of the balloon with precise dosimetry, that is, all three of the regions irradiated have essentially the same amount of radiation absorbed. This provides for uniform treatment of the tissue.

The sequence shown in FIGS. 16A-16C illustrate a three position probe, thus, a handle designed to execute a three position procedure might include three stop points for the axial positioning mechanism. For instance, the handle illustrated in FIG. 13B might be modified to include three notches, rather than two. Furthermore, because the surgeon can see the reddening of tissue being treated as indicated by the lines 912, 913, and the position of the beam because of aim beam technology and the like transmitted down the fiber, the surgeon may manually position the fiber tip to achieve the radiation results desired.

The precise positioning provided by the mechanism according to the present invention, in combination with the cooled saline, and non-compliant balloon provides a superior treatment tool. The cool saline prevents charring so that a greater dose can be delivered to the patient in a given procedure. Furthermore, the direct visualization allows the surgeon to detect when charring begins, or an amount of discoloration indicating necrosis achieved during a given procedure, in order to control the dosimetry.

Figure 17:
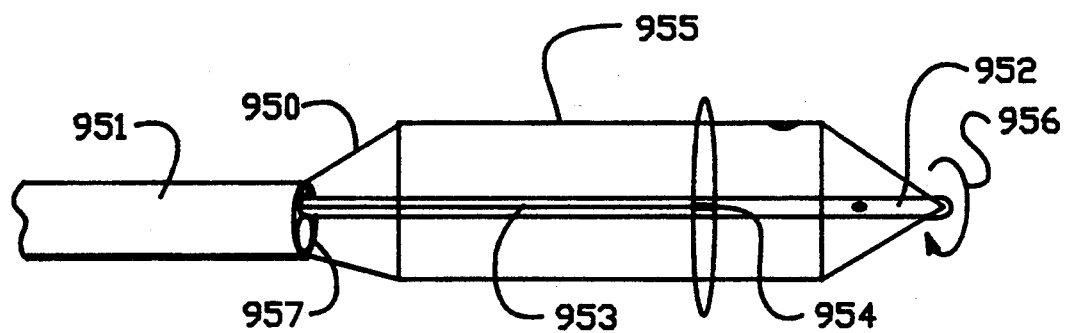
FIG. 17 illustrates operation of the positioning mechanism with a cutting beam in a probe according to the present invention.

FIG. 17 illustrates another use of the precise positioning mechanism of the present invention. As can be seen, a balloon 950 is coupled to a catheter 951. The inner member 952 for positioning the fiber 953 and fiber tip 954 within the balloon 950 is provided. The fiber tip in this embodiment includes a focusing mechanism such as illustrated in FIG. 11. The surgeon may position the fiber tip 954 as indicated, and irradiate a precise circle on the surface 955 of the balloon 950 by actually spinning the fiber 954 as indicated by arrow 956. The cutting action can be precisely controlled, in depth by choosing the balloon size, and in position through direct visualization through scope 957 and precise positioning of the fiber tip 954.

Figure 18:
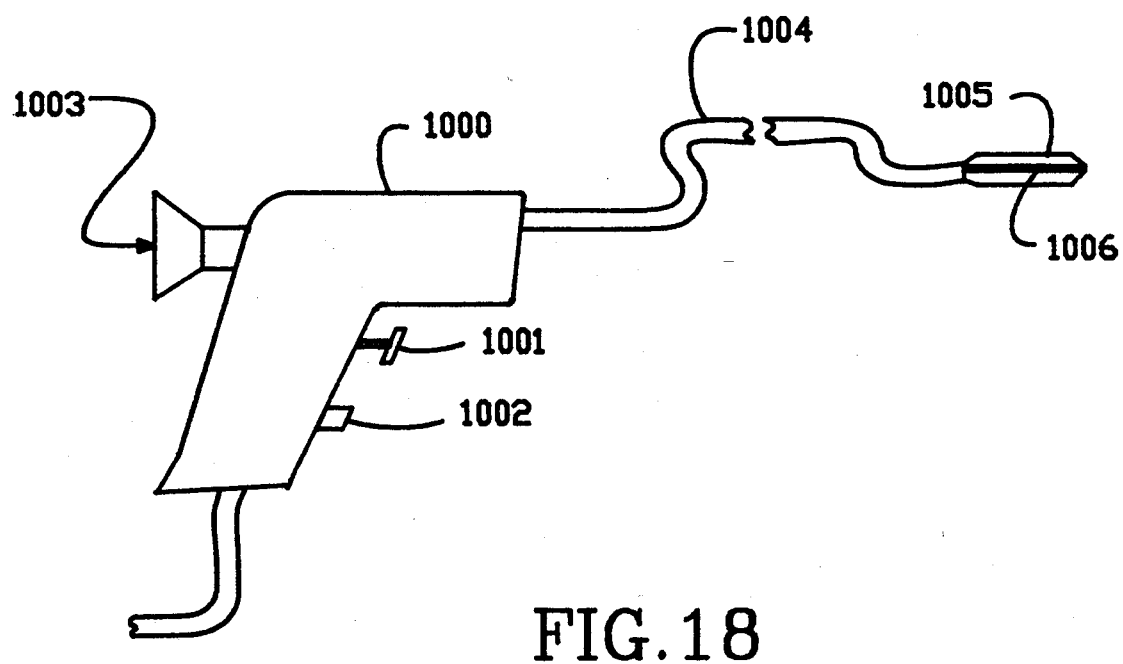
FIG. 18 illustrates a probe according to the present invention using a long, flexible catheter.

FIG. 18 illustrates an alternative embodiment of the present invention in which the catheter is flexible. Thus, a handle 1000 is provided which includes an axial positioning trigger 1001 and a rotational positioning wheel 1002 as described above. A scope 1003 is inserted in the handle 1000 and along the catheter 1004 to balloon 1005. The balloon 1005 includes the positioning mechanism schematically illustrated at 1006 and other features of the tool as described above. A flexible catheter 1004 as illustrated in FIG. 18 may be used in a wide variety of environments other than the urethra. For instance, it may be used in blood vessels or other hollow regions of the body to perform surgical procedures under direct visualization with controlled laser dosimetry. Thus, this probe may be used in the vascular system, including the carotid artery, the aorta, or other coronary vessels. State of the art scope designs provide the ability to insert flexible scopes in the range of a millimeter in diameter into long, flexible catheters 1004. The non-compliant balloon 1005 is used to position the fiber tip under direct visualization in the tissue to be treated, compress the tissue in the region around the fiber, and control the propagation distance of the laser energy from the fiber tip to the tissue. Further, the balloon can be used to circulate cool fluid to keep the temperature of the tissue being treated cool or prevent charring of the tissue during treatment.

An alternative surgical tool for trans-urethral resection of the prostate gland is described with reference to FIGS. 19-23A and 23B, using features without a mechanism for positioning the fiber tip within the balloon. In FIG. 19, a plan view of the surgical tool 1010 is shown. Surgical tool 1010 includes an outer sheath 1020 having a distal end 1012 and a proximal end 1014. As will be described further below, the distal end 1012 is inserted into the urethra of the patient and positioned at a region adjacent to the prostate gland. Preferably, outer sheath 1020 is formed of series 300 stainless steel, and has a circular cross-section (Fig. 22 with a diameter sufficient to support the components of surgical tool 1010 described hereinafter (approximately 0.2 inch).

A cannula 1042 is positioned within sheath 1020. Cannula 1042 has a circular cross-section, a proximal end and a distal end coincident with the proximal end 1014 and distal end 1012 of outer sheath 1020, respectively. Bayonet mount 1021, coupled to proximal end 1014 of sheath 1020, secures cannula 1042 in sheath 1020. Positioning grip 1022 is attached to bayonet mount 1021. Grip 1022 is utilized to allow mount 1021, and cannula 1042, to be secured to outer sheath 1020. Mount 1021 couples about a notched ring 1015 attached to proximal end 1014 of sheath 1020.

An endoscope assembly 1025 is secured to bayonet mount 1021 by a second bayonet mount 1024. Scope assembly 1025 includes an eyepiece 1035 which is offset from axis 1016, where axis 1016 is defined by the length of sheath 1020 at the center point circular cross-section thereof. Scope assembly 1025 includes light channels 1033, 1034, and viewing channel 1032 which are positioned in cannula 1042 and extend from the eyepiece section of scope assembly 1025 to the distal end of sheath 1020 (detailed in FIGS. 20 and 21). Scope assembly 1025 may be of the type manufactured by Carl Storz Endoscopy-America, Inc., Culver City, California. Probe handle 1027 is coupled to scope assembly 1025 by a plastic snap coupling 1026.

A distendable dilation element or balloon 1040 is coupled to distal end of cannula 1042. A cannula probe 1052 is also provided in cannula 1042 and is extendable into balloon 1040 when balloon 1040 is distended. Cannula probe 1052 includes a fiber optic element 1055 (detailed in FIGS. 20-22) for transmitting laser energy to the distal end of the surgical instrument, and laterally providing the laser energy 1047 through balloon 1040 onto the surgical site.

Further, by using an off-axis viewing eyepiece in assembly 1025, element 1055 may be comprised of a thicker fiber optic element than currently employed TURP devices, thereby providing greater efficiency in the delivery of the laser energy to the affected area.

A flexible fiber optic cable and saline supply tube are coupled to probe handle 1027, and are encased in a flexible plastic tube 1028. The fiber optic cable couples a laser energy source 1030 to fiber optic element 1055. The saline supply tube couples a source of pressurized saline 1031 to cannula probe 1052.

Figure 21:
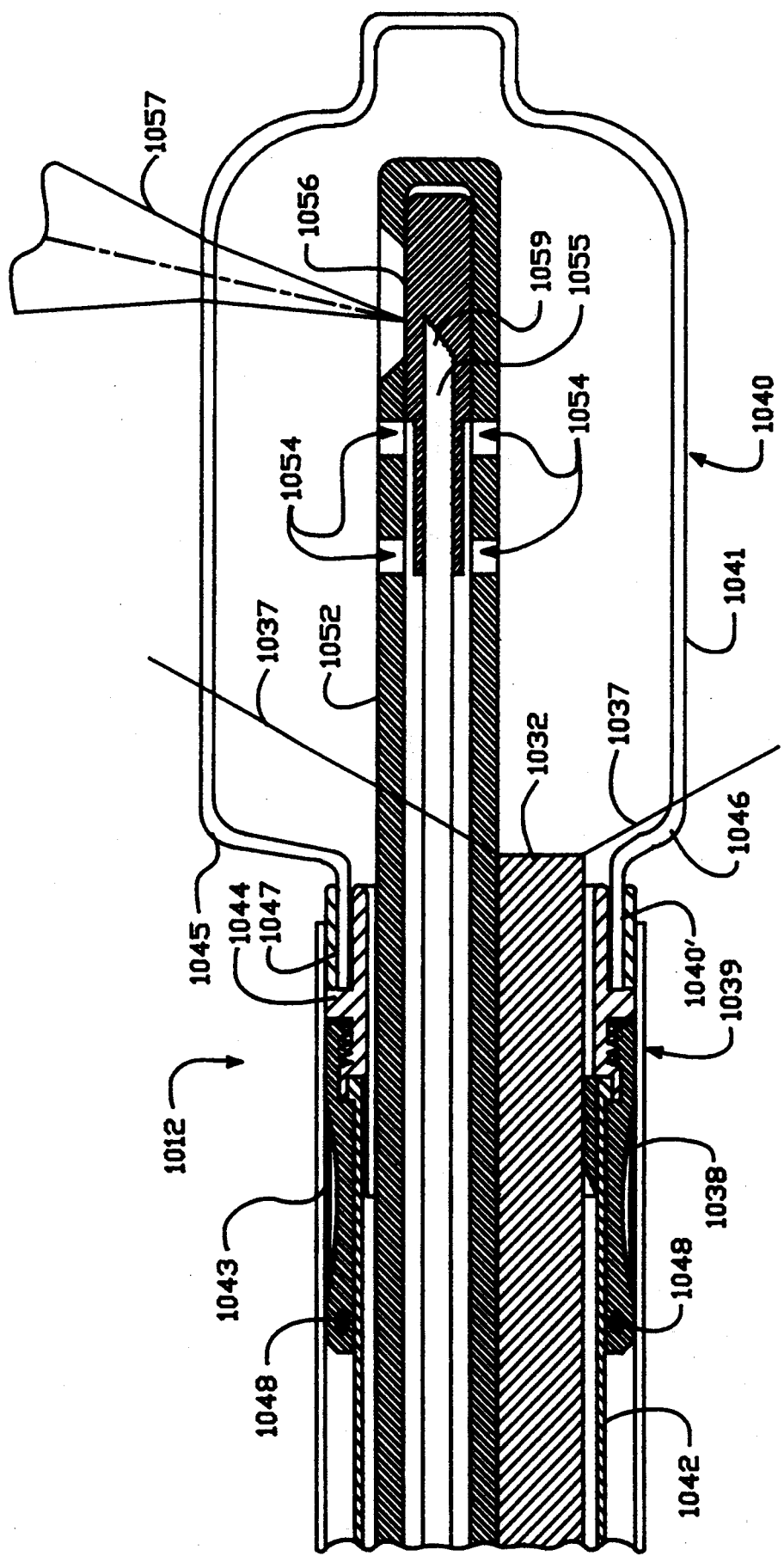

FIGS. 20 and 21 are enlarged, cutaway views of the distal end of surgical instrument 1010.

Inner cannula 1042, positioned within outer sheath 1020, encases light channels 1033, 1034, inner cannula probe 1052, view channel 1032, and cannula probe 1052 with fiber optic element 1055. Balloon 1040 is coupled to distal end of cannula 1042. A lip 1049 is provided at the end of cannula 1042. Prior to surgery, balloon 1040 is attached to balloon attachment sleeve 1044 by placing anterior end thereof around sleeve 1044, and securing support ring 1047 over anterior end and sleeve 1044. A collar 1043, sealed around cannula 1042 by O-ring 1048 positioned in notch 1039, includes a threaded end 1039 which engages a threaded portion of attachment sleeve 1044 to secure balloon 1040 to cannula 1042. Attachment sleeve 1044 includes a key 1038 which inserts into a notch (not shown) in the interior of cannula 1042 to ensure alignment of balloon 1040 with respect to sheath 1020.

Cannula probe 1052 protects fiber optic element 1055 from damage during assembly of surgical device 1010 once outer sheath 1020 is positioned in the urethra. A quartz tip 1056 surrounds the end 1059 of fiber optic element 1055 to hermetically seal the end 1059. This ensures contaminant-free operation of the fiber optic 1055. The end 1059 of the fiber optic is angled to deliver laser energy in a lateral manner 1057 to the region adjacent distal end 1012 of sheath 1020.

Figure 22:
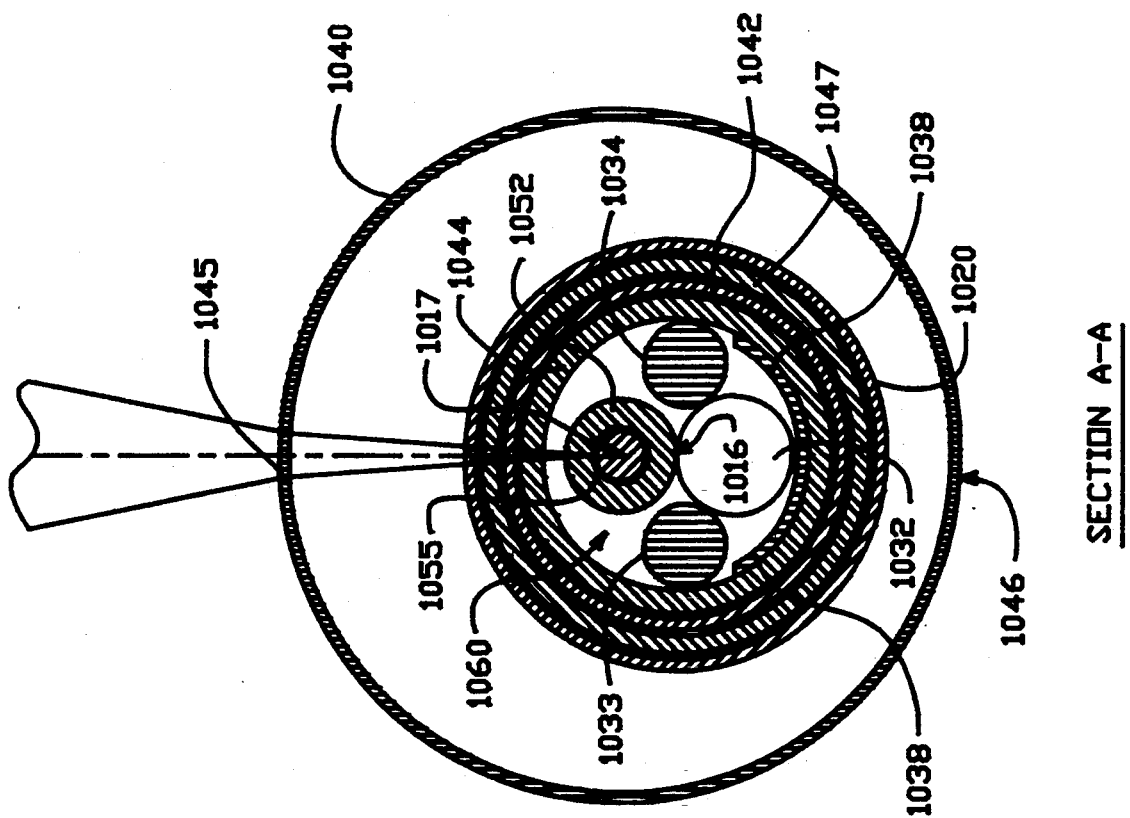
FIG. 22 is a cross-sectional view along line A—A in FIG. 20.

Saline supply 1031 is coupled directly to cannula probe 1052 and provides pressurized saline solution thereto under control of the surgeon. As shown in FIGS. 20–22, fiber optic 1055 has a diameter smaller than the inner diameter of cannula probe 1052, thereby producing a travel path for the pressurized saline into balloon 1040. Saline ducts 1054 are provided in cannula probe 1052 to vent saline solution into balloon 1040. When engaged, pressurized saline is provided into balloon 1040 through inner cannula 1052 to distend balloon 1042 thereby dilating the tissue adjacent balloon 1040. Once the saline solution is provided through ducts 1054, generally when probe 1052 is in the extended position as shown in FIG. 21, balloon 1040 will distend to the shape shown. When the elasticity of the balloon reaches a maximum with respect to the pressure of the saline output through ducts 1054, saline circulates back to an output duct 1029 via a return path through inner cannula 1042 in those areas not occupied by light channels 1033, 1034, cannula probe 1052, or viewing channel 1032; these regions are shown by indicia 1060 in FIG. 22. In this manner, the surgeon can determine the full distension of balloon 1040 when the saline solution is passed through output duct 1029 on handle 1027.

The circulation of saline into the balloon and back via the use of saline return path 1060 allows the continuous flow of saline to the balloon to be monitored and controlled by the surgeon, thereby allowing precise control of the temperature at the operating site to cool the urethral mucosa. With such control, charring of tissue at the operating site is prevented and greater control over the operating procedure is achieved.

As shown in FIG. 21, balloon 1040 includes an anterior portion, which attaches around attachment sleeve 1044, and a cylindrical portion, generally 1041, which has a circular cross-section with a radius extending equidistantly from axis 1017, where axis 1017 is defined by the center point of the circular cross-section, and the length of, cannula probe 1052.

A unique aspect of the present invention is the fact that the circular cross-section of cylindrical portion 1041 balloon 1040 is concentric with respect to axis 1017 defined by cannula probe 1052. This ensures a constant distance between cannula probe 1052 and the surgical area. The cross-section of anterior portion 1041 of balloon 1040 is eccentric with respect to central axis 1016 of sheath 1020, and cannula 1042. As shown in Fig. 22, central axis 1016 is defined at the center point of the circular cross-sections of sheath 1020, and cannula 1042. The radius between the outer surface of the anterior portion 1041 balloon 1040, shown in FIG. 22, and axis 1017, is 0.55 inches. The distance between central axis 1016 and point 1046 of anterior portion 1041 is 0.22 inch, whereas the distance from axis 1016 to point 1045 is about 0.33 inch for a typical transurethral probe. The distance from axis 1016 to posterior portion 40' of balloon 1040 is 0.055 inch.

As shown in FIGS. 20–22, the opening in posterior portion 40' of balloon 1040 is eccentric with respect to the outer diameter of anterior portion 1041.

The shape of balloon 1040, particularly the eccentricity of the anterior portion 1041 of balloon 1040 with respect to anterior portion, allows fiber optic element 1055 to be centered with respect to the dilated area adjacent balloon 1040. Thus, the laser energy 1057 provided through element 1055 is at a constant, equal distance from the point of delivery, tip 1056, to the tissue, providing greater accuracy in the delivery of laser energy to the effected area. In addition, this allows an advantageous arrangement of cannula probe 1052, light channels 1033, 1034, and viewing channel 1032 in cannula 1042, allowing for a single, integrated assembly of the tool once sheath 1020 is in position in the urethra. As noted above, a key 1038 is provided in a notch (not shown) the bottom portion of cannula 1042 to ensure the proper alignment of cannula 1042 and balloon 1040 with respect to the scope assembly 1025 and the distal end 1012 of outer sheath 1020.

In a surgical procedure involving instrument 1010, sheath 1020 is first placed into the urethra with an obturator positioned therein. The obturator (not shown) provides a sealed, rounded endpiece at distal end 1012 of sheath 1020 to allow sheath 1020 to be inserted into the urethra, by ensuring that distal end 1012 of sheath 1020 does not encounter resistance as it passes up the urethra, thereby reducing the risk of injury. Typically, the sheath will be passed into the bladder, the obturator removed, and the catheter passed into the bladder through the sheath. Then the catheter is positioned in the prostate. Ultrasound imaging may be used to position distal end 1012 of sheath 1020 at a region adjacent the prostate gland. Prior to insertion of sheath 1020 into the urethra, balloon 1040 and cannula probe 1052 are provided in cannula 1042; likewise light channels 1033, 1034 and viewing channel 1032, are inserted into cannula 1042 and scope assembly 1025 is coupled to mount 1021 using mount 1024. Once sheath 1020 is positioned in the urethra, the obturator is removed and cannula 1042, including balloon 1040, cannula probe 1052, light channels 1033, 1034 and viewing channel 1032 is inserted into the sheath 1020 and secured by mount 1021. The fiber optic cable, laser source, and saline supply are attached to handle 1027, and handle 1027 attached to scope assembly 1025, prior to attaching scope assembly 1025 to sheath 1020. Once attached, saline solution is directed through ducts 1054 into the balloon thereby distending balloon 1040 to its full shape. Generally, a pressure of approximately 30-60 psi is required to maintain balloon 1040 in its distended state. With the scope attached, viewing channel 1032 and scope assembly 1025 yields a direct view of the procedure at a relatively wide angle, as represented by line 1037. Cannula probe 1052 may be extended, as shown in FIG. 21, or retracted, as shown in FIG. 20, to direct laser energy as desired to the tissue. The angle of viewing channel 1032 (shown generally by lines 1037) allows for a clear view of the entire surgical procedure. Laser energy may be provided by an Nd:YAG laser having an output power of about 40-60 watts. The provision of laser energy to the selected area resulting in coagulation necrosis of the target tissue. The temperature of the circulating saline solution can be constantly monitored during the surgical procedure to maintain a suitable constant temperature at the operating site.

It should be recognized that balloon 1040 may be removed from surgical tool 1010 during certain surgical procedures. In such cases, the laser source may comprise a KTP:YAG laser operating in the 532nm wavelength to enable the surgeon to shear tissue during various types of operating procedures performed percutaneously.

Figure 23A:
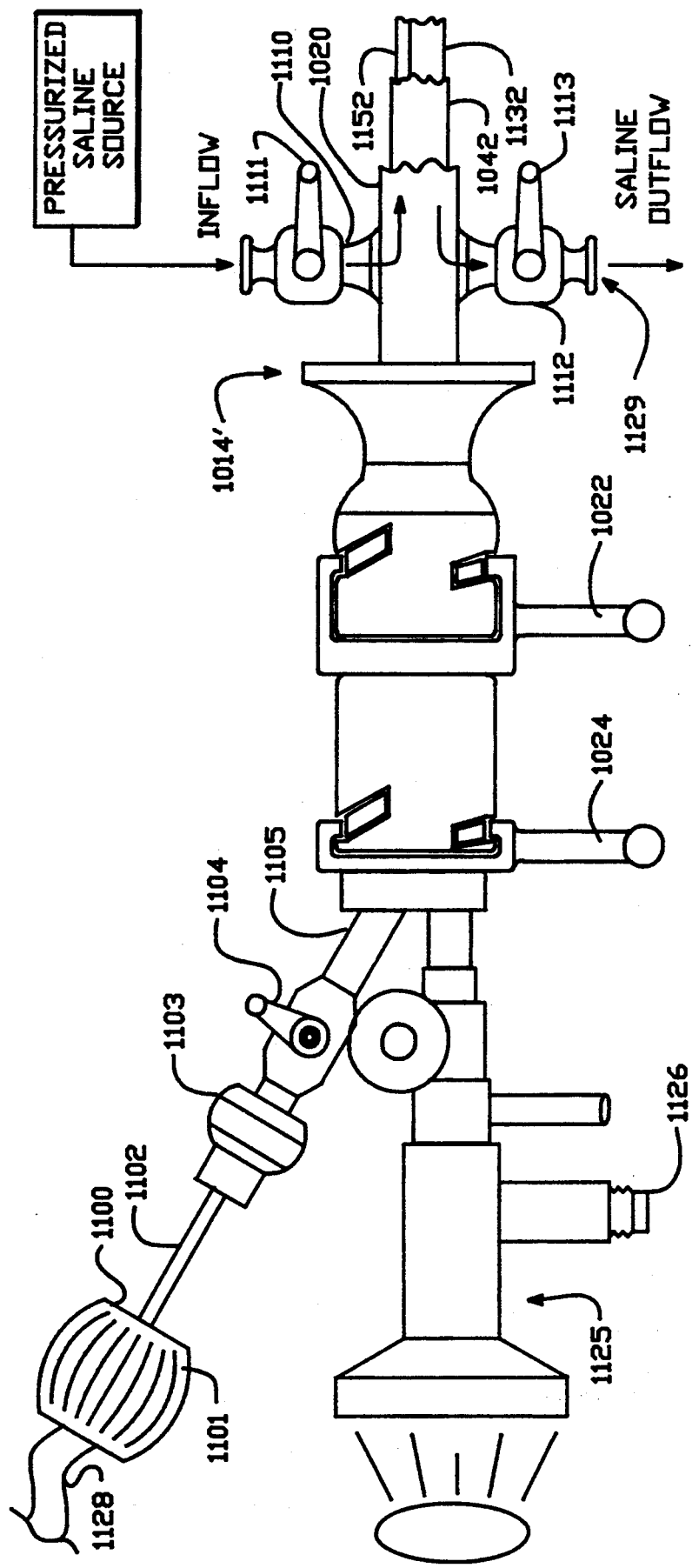
FIG. 23A is an enlarged view of the proximal end of an alternative embodiment of a surgical tool in accordance with the present invention.

FIG. 23A shows (upside down) an alternative embodiment 1010' of the proximal end 1014' of the surgical tool 1010 which utilizes an axial eyepiece, cystoscope assembly 1125 and angled delivery device (ADD) 1100 to provide laser energy to the distal end of surgical tool 1010'. Alternative couplings for providing fluid flow to the distal end 1012' of the instrument 10' are also shown. The axial cystoscope assembly 1125 includes a light source 1126 and a viewing channel 1132 to allow in line viewing of the surgical region at the distal end of surgical tool 1010'. A standard resectoscope such as that available from Carl Stortz, Inc., Germany, is suitable for use with surgical tool 10' Cystoscope assembly 1125 is coupled to bayonet mount 1024. Angled delivery device 1100 includes a handle 1101 which is coupled to a flexible tube 1128 which carries laser energy from a laser energy source, such as an Nd:YAG laser (not shown) to an optical fiber in the ADD 1100. Angled delivery device 1100 further includes a flexible optical fiber 1152, surrounded by an exterior coating 1102 between handle 1101 and gas seal 1103, which is provided through rubber gas seal 1103, valve 1104 and tube 1105 into bayonet mounts 1022, 1024 and sheath 1020. Rubber gas seal 1103 and valve 1104 ensure no leakage from pressurized saline flow input to surgical tool 1010. Saline pressure into cannula 1042 is provided through an input coupling 1110 and output coupling 1112 each having a flow valve 1111 and 1113, respectively. A saline source (not shown) is coupled to fitting 1110 and saline solution is provided into cannula 1042 as described with respect to the embodiment discussed above. Outflow is provided through fitting 1112.

Figure 23B:
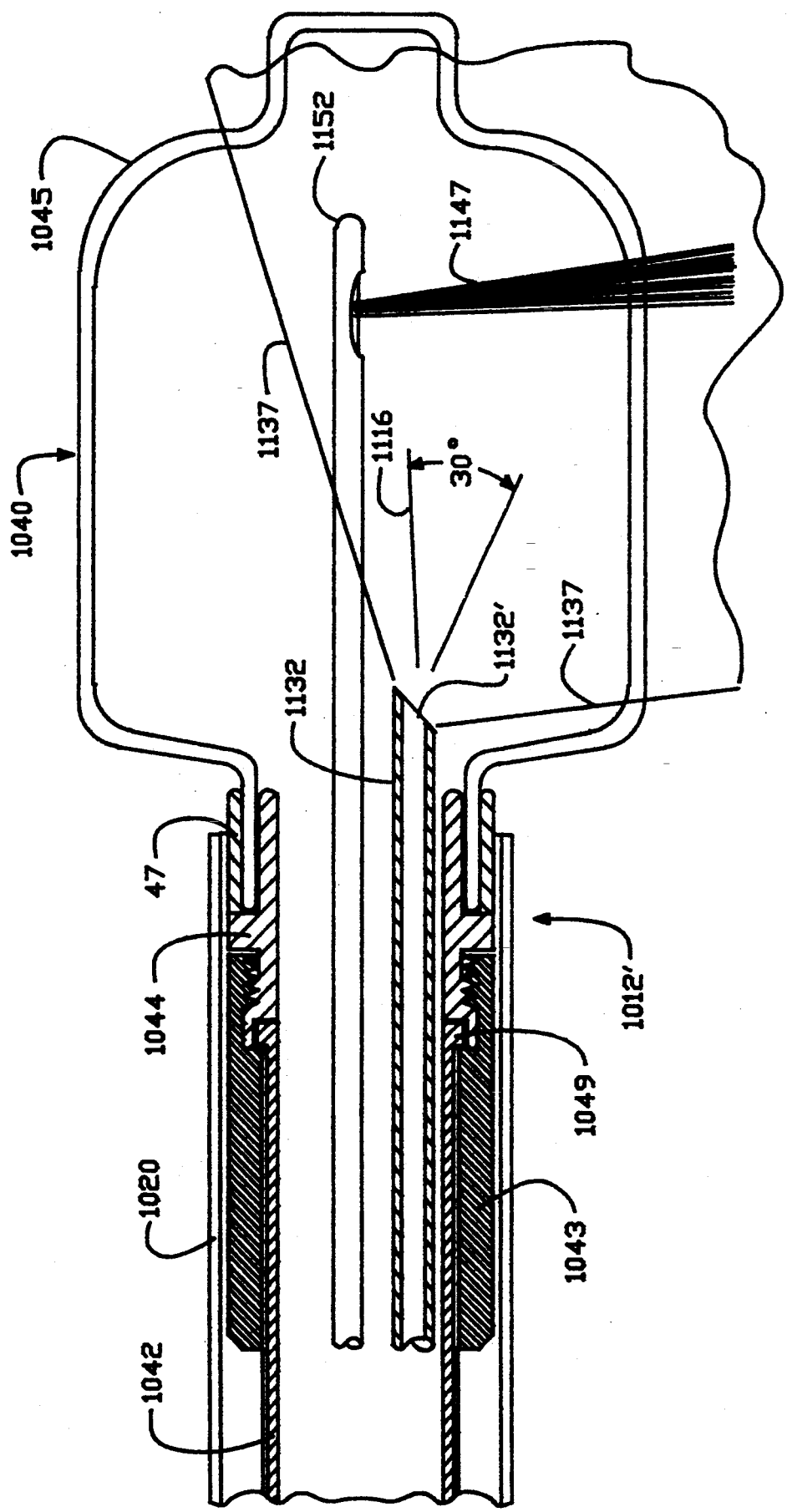
FIG. 23B is an enlarged view of the distal end of an alternative embodiment of a surgical tool in accordance with the present invention.

FIG. 235 depicts distal end 1012' of an alternative embodiment of a surgical device in accordance with the present invention. In particular, viewing channel 1132 of cystoscope assembly 1125 may have either an angled distal end 1132' or a straight 0° field of vision. Although FIG. 235 shows a 30° scope 1132, a 0° scope will likely be better for the preferred system. The scope allows the surgeon to view the surgical site in direct relation to the manner in which laser energy 1147 is provided thereto by the output end of angled delivery device 1100, as defined by lines 1137 depicting the field of view assembly 1125. As depicted in FIG. 23B, cannula probe 1152, coupled to angle delivery device 1100, delivers laser energy 1147 in an angle relationship in a manner similar to that defined with respect to cannula probe 1052, discussed above.

The many features and advantages of the present invention should be obvious to those skilled in the art. For example, it should be readily apparent that the surgical tool 1010 may be adapted for uses other than TURP. In this regard, balloon 1040 is designed to be removable from distal end 1012 of the device to allow the tool to be used in other surgical procedures in fields such as neurosurgery, cardiology, and gynecology. In such instances, the tool is not limited to trans-urethral applications, but may be utilized in any number of translumenal and percutaneous surgical procedures, such as percutaneous ablation of an intrapelvic renal tumor, percutaneous incision of an ureteropelvic junction obstruction, or tissue welding.

In conclusion, a new surgical probe technology is provided for use in confined regions of the body, such as blood vessels, the urethra, the esophagus, and others, based on the utilization of a non-compliant balloon with a direct visualization scope. Also, a fiber optic energy delivery device is coupled with the scope and non-compliant balloon to provide precise dosimetry within confined body regions under direct visualization.

The probe is useful particularly for trans-urethral resection of the prostate, or other techniques based on the use of laser energy to ablate tissue within a hollow vessel, such as angioplasty and the like.

The precise positioning mechanism provided at the tip of the probe for controlling the position of the light emitting tip of the fiber optic provides further advances for surgical probe technology. In particularly, precise positioning allows even distribution of energy, with the repeatability that is necessary for surgical procedures.

In addition to direct visualization, and precise control of energy distribution, the structure of the probe of the present invention provides the ability to control the temperature of the tissue being treated by flowing a cooling fluid through the non-compliant balloon structure. This provides greater flexibility in the types of procedures to which the probe is useful, and with the delivery of laser energy, the cooling of the tissue allows a greater energy dosage to be applied before charring of the tissue occurs.

It also, by its design, separates the circulating fluid from the body. This is important if cooling solutions are used, to prevent large volumes of fluid at cool temperatures from pouring into the patient. It is also important in areas such as brain and blood vessels, to allow good vision without fluid pouring into a confined space.

Also, the tool of the present invention tamponades superficial blood vessels to prevent bleeding that would obscure vision and absorb laser energy thereby preventing the laser energy from penetrating tissue.

A further advantage of the non-compliant balloon structure for use in confined regions arises from the compression of tissue in the confined region upon inflation of the balloon. Thus, in the urethra, the balloon is inflated and prostate tissue around the walls of the urethra is compressed. As has been demonstrated in the prior art with other structures, this compression increases the effective depth of penetration of the laser energy into the prostate, by placing a greater proportion of the prostate gland within the propagation distance of the beam. Furthermore, the compression of the tissue surrounding the non-compliant balloon secures the position of the balloon within the confined region and allows the surgeon a consistent view, with which he or she will become familiar, allowing further improvement in the surgeon's skill in the procedure.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A surgical probe for insertion into a confined region, comprising:
   a multi-lumen catheter having a proximal end and a distal end;
   a transparent balloon coupled to the distal end of the multi-lumen catheter, the balloon having a known shape when inflated to compress tissue in the confined region;
   a direct-visualization scope in a first lumen of the multi-lumen catheter providing direct visualization of the confined region through the balloon;
   a temperature regulated fluid source for providing transparent fluid of a controlled temperature;
   an adaptor, coupled to a second lumen of the multi-lumen catheter near the proximal end, for supplying the temperature regulated transparent fluid from the temperature regulated fluid source through the second lumen to inflate the balloon;
   a laser source producing an output beam; and
   a fiber optic operably attached to the laser source, the fiber optic having a longitudinal axis in a third lumen of the multi-lumen catheter, the fiber optic including a light emitting tip positioned within the balloon to deliver the output beam laterally from the longitudinal axis through the balloon, the temperature regulated fluid inflating the balloon controlling temperature of the light emitting tip during output beam delivery.

2. The surgical probe of claim 1, wherein the balloon has a proximal end coupled to the multi-lumen catheter and a distal end, and further including:
   means, coupled to the third lumen and the distal end of the balloon, for positioning the light emitting tip of the optical fiber within the balloon to establish a known propagation distance to the surface of the balloon for light energy emitted from the light emitting tip.

3. The surgical probe of claim 2, wherein the means for positioning comprises:
   a sheath extending from the distal end of the third lumen to the distal end of the balloon slidably receiving the light emitting tip of the fiber optic.

4. The surgical probe of claim 3, further including a second adaptor coupled to the proximal end of the third lumen for supplying the temperature regulated fluid through the sheath to cool the light emitting tip of the fiber optic.

5. The surgical probe of claim 3, further including:
   means, coupled to the fiber optic, for positioning the light emitting tip longitudinally within the sheath.

6. The surgical probe of claim 4, further including:
   means, coupled to the fiber optic, for rotating the light emitting tip within the sheath.

7. The surgical probe of claim 6, wherein the known shape of the balloon when inflated comprises a cylindrical section, and the sheath lies substantially along the axis of the cylindrical section.

8. The surgical probe of claim 3, further including:
   means, coupled to the fiber optic, for positioning the light emitting tip longitudinally within the sheath; and
   means, coupled to the fiber optic, for rotating the light emitting tip within the sheath.

9. The surgical probe of claim 8, wherein the known shape of the balloon when inflated comprises a cylindrical section having an axis, and the sheath lies substantially along the axis of the cylindrical section.

10. The surgical probe of claim 1, wherein the adaptor coupled to the second lumen provides the fluid at pressure sufficient to compress tissue of the confined region.

11. The surgical probe of claim 1, further including means coupled to the temperature regulated fluid source for controlling the pressure of the fluid to compress tissue of the confined region.

12. The surgical probe of claim 1, further including:
   a pump coupled to the temperature regulated fluid source to control the pressure of the fluid to compress tissue of the confined region.

13. A surgical probe for insertion into a confined region, comprising:
   a multi-lumen catheter having a proximal end and a distal end;
   a transparent balloon having a proximal end coupled to the multi-lumen catheter and a distal end, comprising a non-compliant material having a known shape when inflated:
   a direct-visualization scope in a first lumen of the multi-lumen catheter providing direct visualization of the confined region through the balloon:
   a temperature regulated fluid source for providing transparent fluid of a regulated temperature;
   an adaptor, coupled to a second lumen of the multi-lumen catheter near the proximal end for supplying the temperature regulated transparent fluid from the temperature regulated fluid source through the second lumen to inflate the balloon;
   a laser source producing an output beam;
   a fiber optic operably attached to the laser source, the fiber optic having a longitudinal axis in a third lumen of the multi-lumen catheter and having a light emitting tip positioned within the balloon to deliver light energy laterally from the longitudinal axis to the confined region through the balloon, the temperature regulated fluid inflating the balloon controlling the temperature of the light emitting output beam delivery;
   means, coupled to the proximal end of the multi-lumen catheter and to the fiber optic, for moving the light emitting tip of the fiber optic in the balloon during direct visualization; and
   means, coupled to the third lumen, for positioning the light emitting tip of the fiber optic within the balloon during movement by the means for moving to establish a known propagation distance to the surface of the balloon for light energy emitted from the light emitting tip.

14. The surgical probe of claim 13, wherein the means for moving includes:
   means, coupled to the fiber optic, for positioning the light emitting tip longitudinally within the balloon.

15. The surgical probe of claim 13, wherein the means for moving includes:
   means, coupled to the fiber optic, for rotating the light emitting tip within the balloon.

16. The surgical probe of claim 13, wherein the means for positioning comprises:

a sheath extending from the distal end of the third lumen to the distal end of the balloon slidably receiving the light emitting tip of the fiber optic.

17. The surgical probe of claim 16, further including a second adaptor coupled to the proximal end of the third lumen for supplying the temperature regulated fluid through the sheath to cool the light emitting tip of the fiber optic.

18. The surgical probe of claim 16, wherein the known shape of the balloon when inflated comprises a cylindrical section, and the sheath lies substantially along the axis of the cylindrical section.

19. The surgical probe of claim 16, wherein the means for moving includes:
   means, coupled to the fiber optic, for positioning the light emitting tip longitudinally within the sheath; and
   means, coupled to the fiber optic, for rotating the light emitting tip within the sheath.

20. The surgical probe of claim 19, wherein the confined region is within a hollow vessel and the known shape of the balloon when inflated comprises a cylindrical section adapted to contact an inside wall of the hollow vessel, and having an axis, and the sheath lies substantially along the axis of the cylindrical section.

21. The surgical probe of claim 13, wherein the adaptor coupled to the second lumen provides fluid at pressure sufficient to compress tissue of the confined region.

22. The surgical probe of claim 16, further including means coupled to the fluid source for controlling the pressure of the fluid to compress tissue of the confined region.

23. A surgical probe for insertion into a hollow vessel having an inside wall, comprising:
   a multi-lumen catheter having a proximal end and a distal end;
   a transparent balloon having a proximal end coupled to the multi-lumen catheter and a distal end, comprising a non-compliant material having a surface with a known shape when inflated such that the inside wall of the hollow vessel is compressed against a portion of the surface of the balloon;
   a direct-visualization scope in a first lumen of the multi-lumen catheter providing direct visualization of the hollow vessel through the balloon;
   a temperature regulated fluid source for providing transparent fluid of a regulated temperature;
   an adaptor, coupled to a second lumen of the multi-lumen catheter near the proximal end, for supplying the temperature regulated transparent fluid from the temperature regulated fluid source through the second lumen to inflate the balloon;
   a laser source producing an output beam;
   a fiber optic operably attached to the laser source, the fiber optic having a longitudinal axis in a third lumen of the multi-lumen catheter and having a light emitting tip positioned within the balloon to deliver light energy laterally from the light emitting axis to the hollow vessel through the balloon, the temperature regulated fluid inflating the balloon controlling the temperature of the light emitting tip during output beam delivery; and
   means, coupled to the third lumen, for positioning the light emitting tip of the fiber optic within the balloon including a positioning element for the light emitting tip so that light energy emitted from the light emitting tip directed into tissue of the hollow vessel through the surface of the balloon has a substantially constant power density during rotational and longitudinal positioning of the light emitting tip within the balloon.

24. The surgical probe of claim 23, wherein the known shape includes a cylindrical section having an axis, and wherein the positioning element comprises:
   a sheath extending from the distal end of the third lumen to the distal end of the balloon along the axis of the cylindrical section, slidably receiving the light emitting tip of the fiber optic.

25. The surgical probe of claim 24, further including a second adaptor coupled to the proximal end of the third lumen for supplying the temperature regulated transparent fluid through the sheath to cool the light emitting tip of the fiber optic.

26. The surgical probe of claim 24, further including:
   means coupled to the fiber optic, for moving the light emitting tip longitudinally within the sheath; and
   means, coupled to the fiber optic, for rotating the light emitting tip within the sheath.

27. The surgical probe of claim 23, further including:
   means, coupled to the fiber optic, for moving the light emitting tip longitudinally within the balloon; and
   means, coupled to the fiber optic, for rotating the light emitting tip within the balloon.

28. The surgical probe of claim 23, wherein the adaptor coupled to the second lumen provides fluid at pressure sufficient to compress tissue surrounding the hollow vessel.

29. The surgical probe of claim 23, further including;
   means coupled to the temperature regulated fluid source for controlling the pressure of the fluid to compress tissue surrounding the hollow vessel.

30. A surgical probe for transurethral resection of a prostate gland, comprising:
   a multi-lumen catheter having a proximal end and a distal end;
   a transparent balloon having a proximal end coupled to the multi-lumen catheter and a distal end, comprising a non-compliant material having a surface with a known shape when inflated such that inside walls of the urethra contact a portion of the surface of the balloon;
   a direct-visualization scope in a first lumen of the multi-lumen catheter providing direct visualization of tissue through the balloon;
   a temperature regulated fluid source for providing fluid having a regulated temperature;
   an adaptor, coupled to a second lumen of the multi-lumen catheter near the proximal end, for supplying transparent fluid from the temperature regulated fluid source through the second lumen to inflate the balloon;
   a laser source producing an output beam;
   a fiber optic in a third lumen of the multi-lumen catheter having a longitudinal axis and a beveled light emitting tip positioned within the balloon that laterally directs light energy through the surface of the balloon to tissue to deliver light energy to tissue of the prostate gland through the balloon, the temperature regulated fluid inflating the balloon controlling the temperature of the light emitting tip during output beam delivery; and
   a mechanism, coupled to the third lumen and extending into the balloon, to position the light emitting tip of the fiber optic within the balloon to establish a known propagation distance to the surface of the balloon for light energy emitted from the light emitting tip.

31. The surgical probe of claim 30, wherein the known shape includes a cylindrical section having an axis, and wherein the mechanism to position comprises:
a sheath extending from the distal end of the third lumen to the distal end of the balloon along the axis of the cylindrical section, slidably receiving the light emitting tip of the fiber optic.

32. The surgical probe of claim 31, further including a second adaptor coupled to the proximal end of the third lumen for supplying the temperature regulated fluid through the sheath to cool the light emitting tip of the fiber optic.

33. The surgical probe of claim 30, wherein the mechanism to position includes:
means, coupled to the fiber optic, for moving the light emitting tip longitudinally within the balloon.

34. The surgical probe of claim 30, wherein the mechanism to position includes:
means, coupled to the fiber optic, for rotating the light emitting tip within the balloon.

35. The surgical probe of claim 30, wherein the mechanism to position includes:
means, coupled to the fiber optic, for moving the light emitting tip longitudinally within the balloon; and
means, coupled to the fiber optic, for rotating the light emitting tip within the balloon.

36. The surgical probe of claim 30, wherein the mechanism to position includes a positioning element for the light emitting tip so that light energy emitted from the light emitting tip directed into tissue of the prostate gland through the surface of the cylindrical section of the balloon at a substantially constant power density during rotational and longitudinal positioning.

37. The surgical probe of claim 30, wherein the adaptor coupled to the second lumen provides fluid at pressure sufficient to compress tissue of the prostate gland.

38. The surgical probe of claim 30 further including; means coupled to the temperature regulated fluid source for controlling the pressure of the fluid to compress tissue of the prostate gland.

* * * * *